United States Patent
Achlioptas et al.

(10) Patent No.: US 10,871,459 B2
(45) Date of Patent: Dec. 22, 2020

(54) SYSTEMS AND METHODS FOR MAKING ASSIGNMENTS IN ISOTOPE-LABELLED PROTEINS USING NUCLEAR MAGNETIC RESONANCE DATA

(71) Applicant: The Regents of the University of California, Oakland, CA (US)

(72) Inventors: Demetrios Achlioptas, San Jose, CA (US); Nikolaos G. Sgourakis, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/481,038

(22) PCT Filed: Feb. 17, 2018

(86) PCT No.: PCT/US2018/018536
§ 371 (c)(1),
(2) Date: Jul. 25, 2019

(87) PCT Pub. No.: WO2018/152434
PCT Pub. Date: Aug. 23, 2018

(65) Prior Publication Data
US 2019/0391093 A1    Dec. 26, 2019

Related U.S. Application Data

(60) Provisional application No. 62/460,534, filed on Feb. 17, 2017.

(51) Int. Cl.
*G01N 24/08*    (2006.01)
*G16H 50/70*    (2018.01)
(Continued)

(52) U.S. Cl.
CPC ......... *G01N 24/087* (2013.01); *G01R 33/465* (2013.01); *G06F 16/9024* (2019.01); *G16H 50/70* (2018.01)

(58) Field of Classification Search
CPC .. G01N 24/087; G16H 50/70; G06F 16/9024; G01R 33/465
See application file for complete search history.

(56) References Cited

U.S. PATENT DOCUMENTS 6,677,160 B1 *  1/2004  Stockman ............... C40B 40/04
                                                          435/7.1
8,150,634 B1 *  4/2012  Constantine ........... G16B 15/00
                                                          702/20
(Continued)

FOREIGN PATENT DOCUMENTS

WO    WO 2014-089301 A1    6/2014

OTHER PUBLICATIONS

International Search Report and Written Opinion for PCT/US2018/018536, dated May 21, 2018, 17 pages.
(Continued)

*Primary Examiner* — Gregory H Curran
(74) *Attorney, Agent, or Firm* — Morgan, Lewis & Bockius LLP

(57) ABSTRACT

Computing systems and methods for characterizing a protein are provided. Each residue in a subset of the protein is in an amino acid type set and is represented by a vertex in a graph G formed from an atomic model of the protein. NMR data, acquired with some of the residues of the protein isotopically labeled, is used to form a graph H with each vertex representing a different residue of the protein and assigned one or more amino types. Placements of H onto G are formed, each including mappings assigning vertices in H to vertices in G subject to the constraints that vertices in H mapped to vertices in G cannot be of different amino acid (Continued)

types and edges between pairs of vertices in H must map to corresponding edges in G. For each vertex in H, the number of different valid mappings to G is determined by polling the placements as a constraint satisfaction problem and is deemed assigned when only a single unique assignment is identified.

18 Claims, 16 Drawing Sheets

(51) Int. Cl.
  *G06F 16/901*  (2019.01)
  *G01R 33/465* (2006.01)

(56) References Cited

U.S. PATENT DOCUMENTS

| | | |
|---|---|---|
| 2003/0135331 A1 | 7/2003 | Hogue et al. |
| 2006/0171891 A1* | 8/2006 | Ardenkjaer-Larsen ............ G01N 24/088 424/9.3 |
| 2011/0144065 A1 | 6/2011 | Denaro et al. |
| 2016/0311801 A1 | 10/2016 | Lopez-Tapia et al. |

OTHER PUBLICATIONS

Bermejo et al., "Deuterated protein folds obtained directly from unassigned nuclear overhauser effect data", Journal of American Chemistry Society, 2008, vol. 130, No. 12, pp. 3797-3805.
Wagner and Wüthrich, 1982, J. Mol. Biol., 155, pp. 347-366.
Poulson et al., Biochemistry 19, 1980, pp. 2597-2607.
Bax et al., 1983, "Sensitivity-Enhanced Correlation of $^{15}N$ and $^{1}H$ Chemical Shifts in Natural-Abundance Samples via Multiple Quantum Coherence," J. Am. Chem. Soc. 105, pp. 7188-7190.
Gardner, et al., 1998, "Solution NMR Studies of a 42 KDa *Escherichia coli* Maltose Binding Protein/β-Cyclodextrin Complex: Chemical Shift Assignments and Analysis," J. Am. Chem. Soc. 120(45), pp. 11738-11748.
Simon et al., "Peptoids: A modular approach to drug discovery", Oct. 1992, Proceedings of the National Academy of Sciences USA, vol. 89, No. 20, 9367.
Chin et al., 2003, Science, vol. 301, Issue 5635, 964.
Chin et al., 2003, Chemistry & Biology vol. 10, Issue 6, 511.
Monneau et al., 2016, "Exploiting *E. coli* auxotrophs for leucine, valine, and threonine specific methyl labeling of large proteins for NMR applications," J. Biomol. NMR 65(2), pp. 99-108.
Jones, "De novo protein design using pairwise potentials and a genetic algorithm," 1994, 3: 567-574.
Ponders and Case, 2003, "Force Fields for Protein Simulations," Advances in Protein Chemistry 66, 27-78.
Lovell, 2000, "The Penultimate Rotamer Library," Proteins: Structure Function and Genetics 40, 389-408.
Zwahlen et al., 1998, "An NMR Experiment for Measuring Methyl-Methyl NOEs in $^{13}C$-Labeled Proteins with High Resolution," J. Am. Chem. Soc. 120 (30), pp. 7617-7625.
Rossi et al., 2016, "$^{15}N$ and $^{13}C$-SOFAST-HMQC editing enhances 3D-NOESY sensitivity in highly deuterated, selectively [$^{1}H$,$^{13}C$]-labeled proteins," Journal of Biomolecular NMR, 1-13.
Natarajan et al., 2017, "An allosteric site in the T-cell receptor Cβ domain plays a critical signaling role," Nature Communications, DOI: 10.1038/ncomms15260.
Lipinski, 1997, Adv. Drug Del. Rev. 23, 3.
Stebbins et al., "Crystal Structure of an Hsp90-Geldanamycin Complex: Targeting of a Protein Chaperone by an Antitumor Agent" 1997, Cell 89, 239-250.
Granata, "Characterizing Structure and Free Energy Landscape of Proteins by NMR-guided Metadynamics", Ph.D. thesis, Scoula Internazionale Superiore di Studi Avanzati, Oct. 21, 2013.
Brackman, "NMR Methyl Chemical Shift Assignments of the Hsp90 Chaperone", Thesis, Technische Universität München, Dec. 2013.
Jordan et al., "Specific Isotopic Labeling of Methyl Groups has Extended the Molecular Weight Limits for NMR Studies of Protein Structure and Dynamics", Cambridge Isotope Laboratories, Inc., Applcation Note 16.
Houben et al. "Side chain dynamics monitored by C-13-C-13 cross-relaxation", Journal of Biomolecular NMR, Jul. 2004.
Jackson, "Hsp90: Structure and Function", Top Curr Chem (2013) 328: 155-240.
Monneau et al., "Automatic methyl assignment in large proteinsby the MAGIC algorithm", Journal of Biomolecular NMR, Nov. 2017.
Mitchell et al., "NMR—From Spectra to Structures: An Experimental Approach", Springer, Second Revised and Expanded Edition, 2007.
Prestergard et al., "Sparse Labeling of Proteins: Structural Characterization from Long Range Constraints", J Magn Reson. Apr. 2014 ; 241: 32-40.
Saio et al., "Structural Basis for Protein anti-Aggregation Activity of the Trigger Factor Chaperone", Science. May 9, 2014; 344(6184).
Evangelidis et al., "Automated NMR resonance assignments and structure determination using a minimal set of 4D spectra", Nature Communications, (2018)9:384. DOI: 10.1038/s41467-017-02592-z.
Tang et al., "Protein structure determination by combining sparse NMRNMRNMR data with evolutionary couplings", Nature Methods, vol. 12 No. 8, Aug. 2015.
Tang et al., "Protein structure determination by combining sparse NMRNMRNMR data with evolutionary couplings", Nature Methods, vol. 12 No. 8, Aug. 2015; Supplementary Figures. doi:10.1038/nmeth.3455.
Topspin Users Guide, Bruker BioSpin GmbH, Jan. 31, 2005.
Williams, "NMR studies of mobility within protein structure", Eur. J. Biochem. 183,479-497 1989.
Xiao et al., "Phosphorylation releases constraints to domain motion in ERK2", PNAS, Feb. 18, 2014, vol. 111, No. 7, pp. 2506-2511.
Xiao et al., "Structure-Based Assignment of Ile, Leu, and Val Methyl Groups in the Active and Inactive Forms of the Mitogen-Activated Protein Kinase Extracellular Signal-Regulated Kinase 2", Biochemistry. Jul. 21, 2015; 54(28): 4307-4319.

* cited by examiner

| First data construct / original graph $G$ | ⎫ 20 |
|---|---|
| Vertex 1 | ⎫ 34-1 |
|     Vertex 1 identifier | ⎫ 36-1 |
|     Residue assignment for vertex 1 | ⎫ 38-1 |
|     Amino acid type of assignment | ⎫ 40-1 |
| Vertex 2 | ⎫ 34-1 |
|     Vertex 2 identifier | ⎫ 36-1 |
|     Residue assignment for vertex 2 | ⎫ 38-1 |
|     Amino acid type of assignment | ⎫ 40-1 |
| ⋮ | |
| Vertex R | ⎫ 34-R |
|     Vertex R identifier | ⎫ 36-R |
|     Residue assignment for vertex R | ⎫ 38-R |
|     Amino acid type of assignment | ⎫ 40-R |
| Edge 1 | ⎫ 42-1 |
|     Edge 1 identifier | ⎫ 44-1 |
|     Edge 1 type | ⎫ 46-1 |
|     Vertex 1 identifier | ⎫ 48-1 |
|     Vertex 2 identifier | ⎫ 50-1 |
| Edge 2 | ⎫ 42-2 |
|     Edge 2 identifier | ⎫ 44-2 |
|     Edge 2 type | ⎫ 46-2 |
|     Vertex 1 identifier | ⎫ 48-2 |
|     Vertex 2 identifier | ⎫ 50-2 |
| ⋮ | |
| Edge T | ⎫ 42-T |
|     Edge T identifier | ⎫ 44-T |
|     Edge T type | ⎫ 46-T |
|     Vertex 1 identifier | ⎫ 48-T |
|     Vertex 2 identifier | ⎫ 50-T |
| ⋮ | |

Fig. 1B

| Primary NOE dataset | — 22 |
| --- | --- |
| Diagonal peak 1 | — 52-1 |
|   Diagonal peak identifier 1 | — 54-1 |
|   Residue assignment for peak 1 | — 56-1 |
|   First PPM | — 58-1 |
|   Second PPM | — 60-1 |
| Diagonal peak 2 | — 52-2 |
|   Diagonal peak identifier 2 | — 54-2 |
|   Residue assignment for peak 2 | — 56-2 |
|   First PPM | — 58-2 |
|   Second PPM | — 60-2 |
| ⋮ | |
| Diagonal peak W | — 52-W |
|   Diagonal peak identifier W | — 54-W |
|   Residue assignment for peak W | — 56-W |
|   First PPM | — 58-W |
|   Second PPM | — 60-W |
| Cross peak 1 | — 62-1 |
|   Cross peak identifier 1 | — 63-1 |
|   First PPM | — 64-1 |
|   Second PPM | — 66-1 |
|   Peak volume / intensity | — 68-1 |
|   Identity of first diagonal peak | — 70-1 |
|   Identity of second diagonal peak | — 72-1 |
| Cross peak 2 | — 62-2 |
|   Cross peak identifier 2 | — 63-2 |
|   First PPM | — 64-2 |
|   Second PPM | — 66-2 |
|   Peak volume / intensity | — 68-2 |
|   Identity of first diagonal peak | — 70-2 |
|   Identity of second diagonal peak | — 72-2 |
| ⋮ | |
| Cross peak X | — 62-X |
|   Cross peak identifier X | — 63-X |
|   First PPM | — 64-X |
|   Second PPM | — 66-X |
|   Peak volume / intensity | — 68-X |
|   Identity of first diagonal peak | — 70-X |
|   Identity of second diagonal peak | — 72-X |
| ⋮ | |

Fig. 1C

| | |
|---|---|
| Second data construct / observed graph *H* | ⎰ 24 |
|   Vertex 1 | ⎰ 30-1 |
|     Vertex 1 identifier | ⎰ 98-1 |
|     Possible assignment 1 for vertex 1 | ⎰ 100-1-1 |
|       Amino acid type of assignment | ⎰ 102-1-1 |
|     Possible assignment 2 for vertex 1 | ⎰ 100-1-2 |
|       Amino acid type of assignment | ⎰ 102-1-2 |
|     ⋮ | |
|     Possible assignment W for vertex 1 | ⎰ 100-1-W |
|       Amino acid type of assignment | ⎰ 102-1-W |
|     Cross peak / edge associated with vertex 21 | ⎰ 62-1 |
|   Vertex 2 | ⎰ 30-2 |
|     Vertex 2 identifier | ⎰ 98-2 |
|     Possible assignment 1 for vertex 2 | ⎰ 100-2-1 |
|       Amino acid type of assignment | ⎰ 102-2-1 |
|     Possible assignment 2 for vertex 2 | ⎰ 100-2-2 |
|       Amino acid type of assignment | ⎰ 102-2-2 |
|     ⋮ | |
|     Possible assignment Q for vertex 2 | ⎰ 100-2-Q |
|       Amino acid type of assignment | ⎰ 102-2-Q |
|     Cross peak / edge associated with vertex 2 | ⎰ 62-2 |
|   ⋮ | |
|   Vertex R | ⎰ 30-R |
|   Edge 1 | ⎰ 106-1 |
|     Edge 1 identifier | ⎰ 108-1 |
|     Cross peak represented by edge 1 | ⎰ 62-1 |
|     Edge type of edge 1 | ⎰ 112-1 |
|   Edge 2 | ⎰ 106-2 |
|     Edge 2 identifier | ⎰ 108-2 |
|     Cross peak represented by edge 2 | ⎰ 62-2 |
|     Edge type of edge 2 | ⎰ 112-2 |
|   ⋮ | |
|   Edge T | ⎰ 106-T |
|     Edge T identifier | ⎰ 108-T |
|     Cross peak represented by edge T | ⎰ 62-T |
|     Edge type of edge T | ⎰ 112-T |
|   ⋮ | |

Fig. 1D

A computing system 100 for characterizing a target protein or an interaction of the target protein with an entity is provided. The computing system 100 comprises one or more processors 74 and memory 90/92 storing one or more programs for execution by the one or more processors. The one or more programs singularly or collectively execute a method. In the method a first data construct is formed comprising an original graph G 20 from an atomic model 12 of the target protein. The original graph G comprises a first plurality of vertices 34 and a first plurality of edges 42.

Each residue in a first plurality of residues of the target protein is a member of an enumerated amino acid type set (e.g. ILE, VAL, LEU, ALA, MET, THR). Each respective vertex 34 in G represents a different residue in the first plurality of residues and is further assigned the amino acid type, in the enumerated amino acid type set, of the different residue. Each respective edge 42 in G uniquely represents a pair of vertices in G that are within a threshold distance of each other in the atomic model.

— 202

Each respective edge in graph G is assigned a first edge type when the pair of vertices represented by the respective edge are for a geminal pair of residues in the atomic model and is assigned a second edge type otherwise.

— 203

The enumerated amino acid set consists of two or more of the group consisting of alanine, valine, isoleucine, leucine, methionine, and threonine.

— 204

The enumerated amino acid set consists of three or more of the group consisting of alanine, valine, isoleucine, leucine, methionine, and threonine.

— 206

The enumerated amino acid set consists of four or more of the group consisting of alanine, valine, isoleucine, leucine, methionine, and threonine.

— 208

The target protein comprises 50, 100, 150, 200, 250, 300, 350, or 400 amino acid residues.

— 210

The atomic model of the target protein includes spectroscopically determined coordinates for each atom of all or a portion of the target protein.

— 212

The coordinates for each atom of the target protein or the portion of the target protein are determined by nuclear magnetic resonance, x-ray crystallography, or electron microscopy.

— 214

The atomic model of all or a portion of the target protein is determined from homology modeling of spectroscopically determined atomic coordinates of all or a portion of one or more second proteins other than the target protein.

— 216

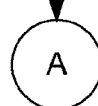

Fig. 2A

Identify a plurality of cross peaks in the primary NOE dataset 22. Each respective cross peak 62 in the primary NOE dataset is generated by NOE interaction between an isotopic label in a different first residue and an isotopic label in a different second residue in the second plurality of residues. ⟶ 270

> The plurality of cross peaks comprises 10, 20, 30, 40, 50, 60, 70, 80, 90, 100, 110, 120, 130, 140, or 150 cross peaks. ⟶ 272

> Each residue in the second plurality of residues is $^{13}C$ isotopically labeled at a single methyl in the side chain of the residue. The identifying 270 comprises (i) identifying a plurality of C, C, H triplets in the primary NOE dataset. Each triplet is formed from (a) an interaction between a first $^{13}C$ labeled carbon in a methyl in a side chain of a first residue and a proton covalently bound to the first $^{13}C$ labeled carbon and (b) an interaction between the first $^{13}C$ labeled carbon and a second $^{13}C$ labeled carbon in a methyl in a side chain of a second residue. Symmetry filter the triplets thereby identifying a reduced set of triplets. Cluster the triplets in the reduced set using the second and third coordinates of each triplet in the reduced set thereby forming a plurality of clusters of triplets. Each respective cluster of triplets is deemed to be a cross peak in the plurality of cross peaks. ⟶ 273

Form a second data construct 24 comprising an observed graph $H$ from the plurality of cross peaks 62. The observed graph $H$ comprises a second plurality of vertices and a second plurality of edges. Each respective vertex 30 in the second plurality of vertices represents a different residue in the second plurality of residues. Each respective edge 106 in the second plurality of edges represents a corresponding cross peak 62 in the plurality of cross peaks. Each respective vertex 30 is assigned one or more amino types in the enumerated amino acid type set using amino acid type assignments made by the primary NOE dataset or one or more secondary NMR datasets taken of the target protein. ⟶ 274

> Each respective edge 106 is assigned the first edge type or the second edge type. ⟶ 275

>> A respective edge in the second plurality of edges is assigned a first edge type when the cross peak in the plurality of cross peaks corresponding to the respective edge satisfies an intensity threshold and is otherwise assigned the second edge type. ⟶ 276

> The second plurality of vertices of the observed graph $H$ is less than the first plurality of vertices of the original graph $G$. ⟶ 277

> At least one vertex 30 in the second plurality of vertices of the observed graph $H$ is assigned two or more amino types in the enumerated amino acid type set using amino acid type assignments made by the primary NOE dataset 22 or one or more secondary NMR datasets taken of the target protein. ⟶ 278

Fig. 2D

```
┌─────────────────────────────────────────────────────────────────────────┐ ╭ 279
│ Create a plurality of placements of the observed graph H onto the       │
│ original graph G. Each respective placement 114 in the plurality of     │
│ placements (i) includes a plurality of mappings and (ii) maps all the   │
│ vertices of the observed graph H onto different vertices in the original│
│ graph G. Each mapping 97 in the plurality of mappings assigns a vertex  │
│ 30 in the observed graph H to a vertex 34 in the original graph G. Each │
│ respective placement in the plurality of placements is subject to a set │
│ of constraints including the constraint that, when a vertex v in the    │
│ observed graph H 24 is mapped to a vertex w in the original graph G 20, │
│ the amino acid type assigned vertex w in the original graph G is in the │
│ one or more amino acid types assigned vertex v. The set of constraints  │
│ further requires that, for an observed edge {a, b} between a vertex a   │
│ and a vertex b in the observed graph H, when vertex a is mapped to a    │
│ vertex v and vertex b is mapped to a vertex w in the original graph G,  │
│ there exists an edge {v, w} between the vertex v and the vertex w in    │
│ the original graph G.                                                   │
│  ┌───────────────────────────────────────────────────────────────────┐  │ ╭ 280
│  │ The set of constraints further requires that, when the observed   │  │
│  │ edge {a, b} in the observed graph H is assigned the first edge    │  │
│  │ type, the edge {v, w} in the original graph G is also assigned    │  │
│  │ the first edge type.                                              │  │
│  └───────────────────────────────────────────────────────────────────┘  │
│  ┌───────────────────────────────────────────────────────────────────┐  │ ╭ 281
│  │ The threshold distance used for identifying edges between         │  │
│  │ vertices 34 in the original graph G is initially 10 Å.            │  │
│  │  ┌─────────────────────────────────────────────────────────────┐  │  │
│  │  │ The threshold distance is increased from the initial        │  │  │ ╭ 282
│  │  │ distance to a larger distance when the creating 254 fails   │  │  │
│  │  │ to create a first threshold number placements for the       │  │  │
│  │  │ plurality of placements. The threshold distance is          │  │  │
│  │  │ decreased from the initial distance to a smaller distance   │  │  │
│  │  │ when the creating 254 creates more than a second threshold  │  │  │
│  │  │ number placements for the plurality of placements.          │  │  │
│  │  └─────────────────────────────────────────────────────────────┘  │  │
│  └───────────────────────────────────────────────────────────────────┘  │
└─────────────────────────────────────────────────────────────────────────┘
                                    │
                                    ▼
┌─────────────────────────────────────────────────────────────────────────┐ ╭ 283
│ Initialize each set in a plurality of sets 32, each set 32 in the       │
│ plurality of sets representing a different vertex 30 in the observed    │
│ graph H.                                                                │
└─────────────────────────────────────────────────────────────────────────┘
                                    │
                                    ▼
┌─────────────────────────────────────────────────────────────────────────┐ ╭ 284
│ Determine, for each respective set 32 in the plurality of sets, a       │
│ number of different mappings for the vertex i 30 represented by the     │
│ respective set in the observed graph H into the original graph G by     │
│ polling the plurality of placements as a constraint satisfaction        │
│ problem in which, for each respective possible assignment of the vertex │
│ i into the original graph G, when a determination is made that there    │
│ exists a mapping 97 in the plurality of mappings that includes the      │
│ respective assignment, the respective set 30 is advanced, and is not    │
│ advanced otherwise.                                                     │
└─────────────────────────────────────────────────────────────────────────┘
```

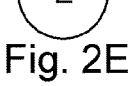

Fig. 2E

| | |
|---|---|
| Deem a vertex 30 in the observed graph H to be uniquely assigned to a vertex 34 in the original graph G when the set 32 for the respective vertex 30 includes a single unique assignment upon completion of the determining 284. | 286 |
| Uniquely assign at least forty, fifty, sixty, seventy, or eighty percent of the vertices 30 in the observed graph H to the original graph G. | 288 |
| The entity is a second protein that binds with target protein and block 286 identifies a portion of a surface of the target protein that is bound by the second protein. | 290 |
| The entity is an inhibitor that binds with target protein and block 286 identifies a portion of a surface of the target protein that is bound by the inhibitor. | 292 |
| The inhibitor has a molecular weight of less than 5000 Daltons. | 294 |
| The inhibitor is a chemical compound that satisfies at least three, at least four, or all five of the Lipinski rule of five criterion. | 296 |
| Use the unique assignment of a first vertex 30 in the observed graph H to the original graph G to assign a first peak in the NOE dataset to a first residue in the atomic model and a second peak in the NOE dataset to a second residue in the atomic model. The first peak and the second peak are not within the plurality of cross peaks and a label of the first residue and a label of the second residue are deemed to create the cross peak in the plurality of cross peaks represented by the first vertex. | 298 |

Fig. 2F

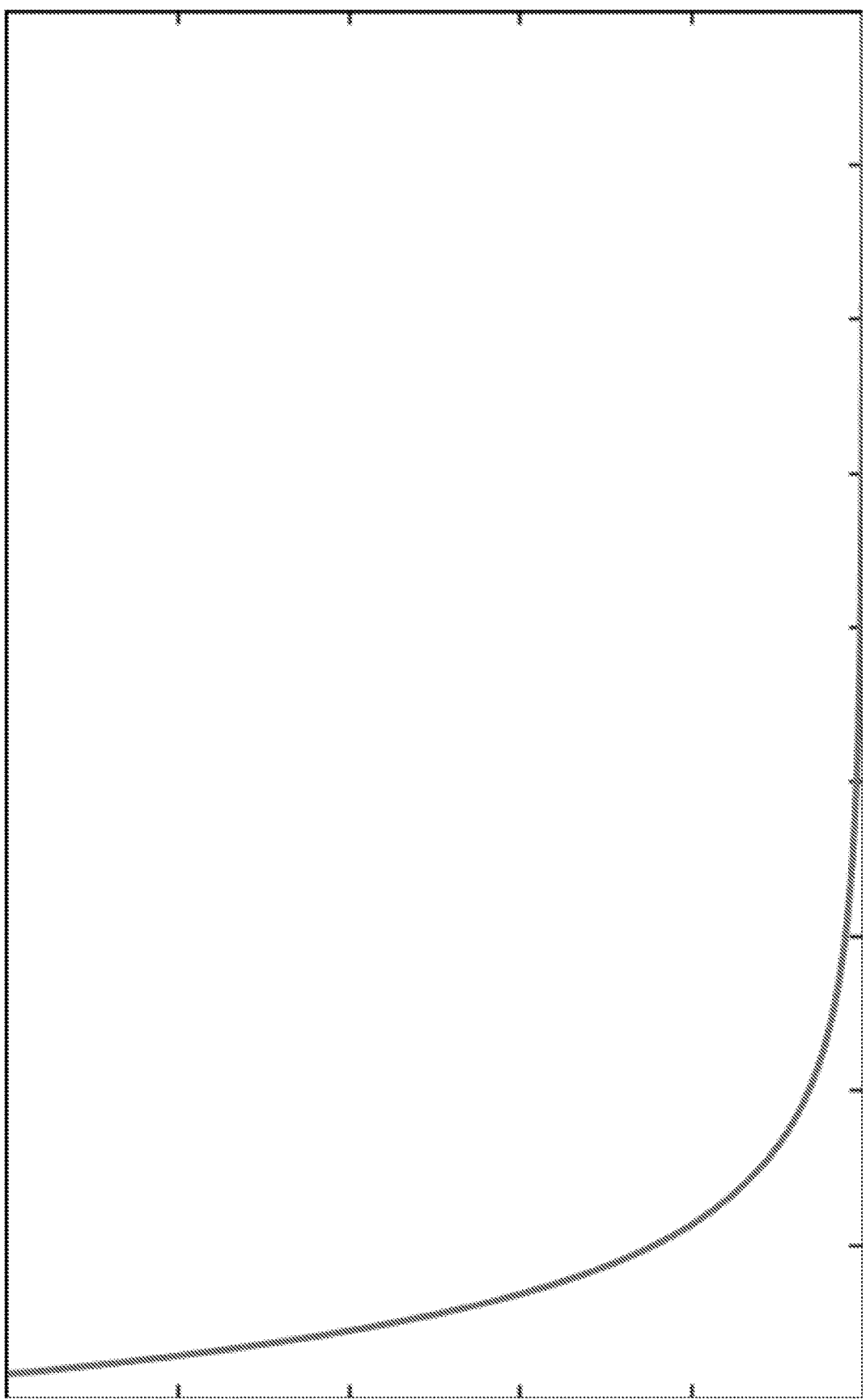

| Column 1 | Column 2 | Column 3 | Column 4 | Column 5 | Column 6 |
|---|---|---|---|---|---|
| a →1 | b →2 | c →3 | d →4 | e →5 | f →6 |
| a →3 | b →2 | c →1 | d →4 | e →5 | f →6 |
| a →3 | b →2 | c →1 | d →4 | e →6 | f →5 |
| a →1 | b →3 | c →2 | d →4 | e →5 | f →6 |
| ⋮ | ⋮ | ⋮ | ⋮ | ⋮ | ⋮ |
| a →1 | b →4 | c →3 | d →2 | e →5 | f →6 |
| S(1) | S(2) | S(3) | S(4) | S(5) | S(6) |

Fig. 6

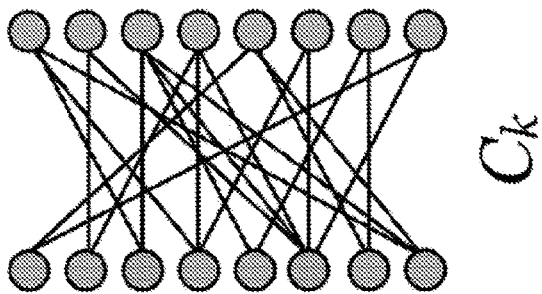
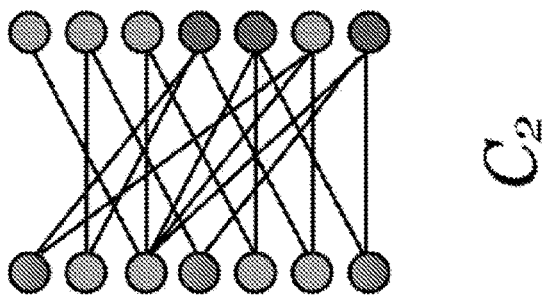
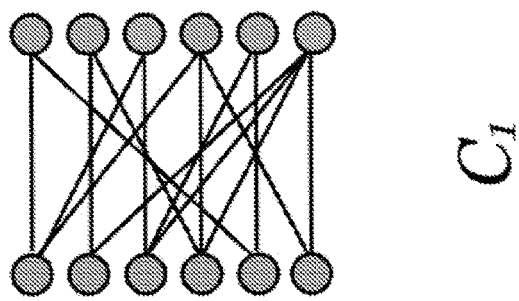
Fig. 7

SYSTEMS AND METHODS FOR MAKING ASSIGNMENTS IN ISOTOPE-LABELLED PROTEINS USING NUCLEAR MAGNETIC RESONANCE DATA

CROSS REFERENCE TO RELATED APPLICATION

The present disclosure claims priority to U.S. Provisional Patent Application No. 62/460,534, entitled "SYSTEMS AND METHODS FOR ASSIGNMENT OF METHYL GROUPS IN ISOTOPE-LABELLED POLYMERS USING NUCLEAR OVERHAUSER EFFECT DATA," filed Feb. 17, 2018, which is hereby incorporated by reference.

TECHNICAL FIELD

The present disclosure relates generally to systems and methods for automated assignment of isotopically labeled groups in a selectively isotope-labelled target protein using a predetermined three-dimensional structure of the target protein and nuclear magnetic resonance (NMR) data of the target protein.

BACKGROUND

Nuclear Overhauser enhancement (NOE) measurements provide an important tool for assigning the $^1$H NMR spectra of polymers. See Wagner and Wuthrich, 1982, J. Mol. Biol. 155, pp. 347-366. The existence of an Overhauser effect between a pair of protons, detected by one or two-dimensional techniques, establishes them as close together in the protein structure. See Withrich, *NMR of Proteins and Nucleic Acids*, John Wiley & Sons, New York, 1986, Chapter 6.

In a simple case, where initial rate measurements are possible and where the spin system can be described as undergoing simple isotropic motion, the relative magnitudes of NOE effects depend on $1/r^6$, where r is the distance separating the two protons. See Poulson et al., 1980, Biochemistry 19, pp. 2597-2607. In proteins, however, there are deviations from this simple case. It is generally not possible to measure detailed time dependences of NOE effects for any except the closest protons within a protein because of the large number of spins in the system and because the signal-to-noise ratio is rarely adequate. In addition, the existence of internal motions within the protein causes variations in effective correlation times for different pairs of protons in the protein. See, Delepierre et al., 1981 in: Biomolecular Stereodynamics (Sarma, R. H. ed.) Academic Press, New York.

Nevertheless, theoretical analysis and experimental results demonstrate that there is a high correlation between the magnitude of the NOE effect and interproton distance of protons in a molecule. As such, NOE measurements provide an important tool for structural studies such as the identification of interactions between proteins and other proteins that elucidate important in vivo signal pathways. NOE measurements also provide an important tool for structural studies such as the study of interactions between proteins and other molecules that selectively bind to such proteins. One such example arises in the case where a small molecule inhibitor binds to a protein. In such instances, NOE measurements can be used to determine exactly where on the protein's surface the small molecule binds, and the specific intermolecular interactions that form between the small molecule inhibitor and the protein. Such information can be used to design inhibitors that have a lower binding coefficient and/or that are more selective to the target protein as compared to related proteins. For instance, in the case of a kinase inhibitor binding to a select kinase (e.g., P38), the NOE measurements can be used to determine how the kinase inhibitor binds to the select kinase. Such information can then be used in structural modeling to design derivatives of the original kinase inhibitor that have an improved binding coefficient for the target kinase and that do not bind similar kinases.

The rate limiting step in the aforementioned structural studies tends to be obtaining assignment information from the NOE measurements. That is, assigning NOE peaks in an NMR spectrum to specific protons, nitrogens, or carbons in the protein or protein complex under study. For many proteins, it is not yet feasible to obtain a complete a description of the NMR spectrum. This hampers NOE assignment because the spectra does not include data for the entire protein. Moreover, regardless of completeness of the NOE data, the NOE data contains many peaks. In typical instances, it takes months of skilled labor to elucidate and assign these peaks to specific protons, nitrogens, or carbons in the target system under study. Automated approaches for such analysis have been developed but such approaches to date remain unsatisfactory.

Studying Polymers Via Nuclear Magnetic Resonance (NMR).

A target protein can be conceptualized as a linear sequence of different block types (each block type being one of the twenty naturally occurring amino acids) of different "shapes," that folds into a well-defined object in space (termed herein a "structure"). Consider the case where the target protein has a known three dimensional structure. That is, the three-dimensional coordinates of the center of each block piece with respect to each other, or on some absolute scale, are determined. An important aspect of understanding what a protein "does" amounts to understanding how it interacts with different molecules in its environment. In particular, of primary importance are interactions that amount to "attachment," in which a small molecule (relative to the size of the protein itself) binds to a specific location on the three-dimensional structure of the protein. While it is known that the small molecule attaches, it is not known where on the surface of the target protein it attaches. The goal in one use case is to find out. While this is not the only relevant use case scenario, it is illustrative. One approach to solving the above problem is to install sensors all over the protein that detect the attachment of the small molecule using conventional methods.

The Chemistry Part. Sticking with the block type analogy, imagine that to synthesize the protein of interest, twenty bins are arranged and each one is filled with a number of identical block pieces such that different bins contain pieces of different shapes. A selected bacterium feeds from these bins. The bacterium ingests the block pieces, assembles them into the protein of interest inside itself, and then excretes the protein. The way that the sensors are installed in this analogy is by selecting some of the bins and replacing all the pieces inside them with pieces that are identical in shape with the pieces removed but are modified to have an embedded "sensor" (e.g., by isotopically labeling these pieces). The sensors are tiny and "inside" each piece, so that the bacterium cannot feel the difference between the original and the modified pieces and synthesizes the protein just as before.

What is a sensor? The word "sensor" as used here is an "environment-sensitive tone generator." Each sensor produces a simple constant sound, e.g., a tone, that depends on:

(i) the shape of the block piece P carrying the sensor, (ii) the set A of block pieces attached to block piece P, (iii) the set N of block pieces attached to the pieces in the set of block pieces A, and (iv) the location and orientation of the block piece within the larger three dimensional structure of the target protein. Points (i) through (iv) are referred to as the "environment" of the sensor.

The AMR Part. After the sensors/tone generators are installed on the target protein, it is now emitting a "chord," consisting of as many notes (tones) as the number of sensor-carrying block pieces in the target protein. To hear the chord, a solution of the target protein is place in a Nuclear Magnetic Resonance (NMR) spectroscopy machine. In the analogy, the NMR machine plays the role of a microphone. Then, in a solution containing the small chemical compound that is known to bind to the target protein, the tone generators in the portion of the surface the protein's area of attachment will be "modified" by the attachment, causing the corresponding sensors to emit a different tone. As a result, by comparing the two chords (before and after binding of the small molecule) it can be determined which sensors were affected by the attachment event. After comparing the two chords (before and after attachment of the small molecule to the target protein) it is not known where on the target protein the attachment occurred because it is not known which sensor (block piece) is producing which tone. In other words, the sensors that are affected by the binding event have not been assigned to specific block pieces. So, even though one can determine which tones were modified due to the attachment event, this does not inform which sensors (block pieces) these tones correspond until the assignment problem is addressed.

The assignment problem. To form a good mental model of the assignment problem, consider an atomic model of the target protein, e.g., the entire block piece assemblage. Which block pieces in the assemblage have been modified to produce sound is known (namely, all the pieces of the chosen particular shapes). Consider further that if someone were to play a tone and then point to a sound-producing block piece in the target protein, one could make a reasonable but far from conclusive estimate of the likelihood that the piece produces that tone. Meanwhile, in the background, the chord of the protein in the NMR solution is playing constantly. The task is to "assign" (map) each tone in the protein's chord to a specific sound-producing block piece. Notably, highly combinatorial thought processes for addressing this assignment problem could be invoked, similar to solving a puzzle. For example, even though some tone T may map "very well" to block piece A but only "well" to block piece B, it can be that the correct thing to do is to map T to B instead of A, because there is some other tone $T_0$ for which A is the only realistic possibility. In fact, far more sophisticated inferences than this are required to solve this assignment problem, very much akin to solving a Sudoku puzzle.

Conventional NMR.

The study of polymers in the manner described so far began in the late 1960s by installing sensors in all of the bins concurrently. Specifically, the first "sensors" amounted to modifying the amide group (N—H) of each residue in the target protein so that the nitrogen (N) atom is replaced with its stable isotope, $^{15}N$. That modification "activates" the nitrogen from being silent to emitting a tone, as described above. During the 1980s and 1990s, several methods for assigning the amides were established, primarily by the National Institute of Health group of Ad Bax (e.g., Bax et al., 1983, "Sensitivity-Enhanced Correlation of $^{15}N$ and $^{1}H$ Chemical Shifts in Natural-Abundance Samples via Multiple Quantum Coherence," J. Am. Chem. Soc. 105, pp. 7188-7190) and this is now considered a straightforward, albeit laborious, task for small to medium-sized protein targets.

One thing that complicates the assignment problem is that each sensor does not emit a pure tone, e.g., a single frequency, but a "mini-chord" of tones, consisting of a primary (loudest) tone and several weaker tones of frequencies slightly lower and slightly higher than the primary tone. A "microphone" (e.g., the NMR spectrometer) captures the sum of all the mini-chords emitted by the sound-producing block pieces. As a result, when there are more and more sound-producing block pieces, e.g., as larger polymers are considered, the amount of "spectral overlap" increases, making it increasingly harder to resolve the primary frequencies within the overall chord.

Another thing that complicates the assignment problem is that, as the size of the target protein considered increases, the intensity of the generated tones decreases. As a result, at some size of the target protein, the intensity of the sensor-emitted tones becomes indiscernible from background noise. As such, using presently known techniques, amide-sensor based NMR is largely infeasible for target proteins with more than 500 residues (50 kDa) at room temperature.

Methyls. Amides are not the only sensors that can be used in a target protein. The main alternative isotopic labeling strategy is to label methyls, which arise in six of the naturally occurring amino acids used to form a protein. As such, for methyl labeling, one targets only a set of 3-6 (typically 4) block type bins, selectively, but this time modifies the methyl group ($CH_3$) of each block piece so that the $^{12}C$ carbon atom is replaced with its stable isotope $^{13}C$. Methyls have one advantage and one disadvantage relative to amides.

The good: Methyls-tones are much louder. As a result, methyls are much better sensors, since the difference in the protein chord caused by attachment can be heard far more clearly. This makes them significantly more useful in biomedical research applications because, for all sensors, loudness is proportional to the amount of protein in the sample. If the sensors are not loud enough, it takes milligram quantities of purified material to be heard, something that becomes prohibitive for larger polymers that are interesting as therapeutic targets.

The bad. Methyls are much harder to map, e.g., the assignment problem for methyls is much harder. To give some perspective, the fact that methyls are much louder than amides was already predicted via mathematical calculations in the late 1960s. But it was not until 1998 that methyl based sensing, e.g., solving the "methyl assignment" problem, was achieved for a large protein molecule. See, Gardner, Zhang, Gehring, and Kay, 1998, "Solution NMR Studies of a 42 KDa *Escherichia Coli* Maltose Binding Protein/β-Cyclodextrin Complex: Chemical Shift Assignments and Analysis," J. Am. Chem. Soc. 120(45), pp. 11738-11748, in which the Maltose Binding Protein, having a molecular weight of 42 kDa, with 370 residues and 118 methyls, was solved by this isotropic labeling technique. As such, the methyl map of a target protein is preferable to its amide map, but is harder to assign.

Three methods, discussed in turn below, have been developed to address the methyl assignment problem.

Original Methyl Assignment: Through-the-Bond Transfer.

In this method, one uses both amide and methyl sensors. The amides are mapped first, using conventional NMR methods. The amide map is then used as a "rough plan" that dramatically simplifies the assignment (mapping) of the methyls (via a phenomenon called "through-the-bond transfer"). This assignment method has two disadvantages. First, the method still needs to form the amide map, and thus the method is largely infeasible for proteins that are larger than 50 kDa at room temperature. Second, solving the methyl assignment problem using amides involves a standardized, but laborious, process, requiring one to two months of data collection and human time on average.

One-at-a-Time Replacement.

In this isotopic labeling method, one simplifies the methyl assignment problem at the expense of increased chemical complexity. Specifically, one picks a specific block piece (not block type) in the entire protein and equips it with a tone generator. Thus, the methyl assignment problem is greatly simplified as one can directly hear the generated tone. In reality, the situation is more complicated than this, in particular, one silences the targeted block piece instead, but this exposition is good enough to establish the point. The drawback with this assignment method is that one needs to repeat this process, e.g., the chemical synthesis and the NMR experiment, for every single methyl, e.g., 100-500 times for target proteins. This one-at-a-time replacement approach is so labor intensive that it can realistically only be carried out using robots, a path that has been reduced to practice by the French company NMR-BIO. The need for such substantial hardware infrastructure means that the approach is only commercially viable as a service, and thus requiring the shipment of samples. Another a drawback with this assignment approach is that the target protein must be producible in very large quantities, since a separate target protein sample and NMR experiment is needed per methyl, by a method that allows the endowment of specific methyls with tone-generating capacity. This rules out a large number of life-sciences-interesting target proteins.

The Nuclear Overhauser Effect.

So far, isotopic labeling techniques that consider tone-generating blocks and the spectrum of the resulting tones have been discussed. In the third approach, pairs of tone-generating blocks interacting via the Nuclear Overhauser Effect (NOE) resulting in an NMR-measurable quantity are exploited. Keeping to the tone-generation analogy, one can think of the "NOE sound" generated by a particular pair of block pieces as a "harmonic." The intensity of each generated harmonic depends strongly on the distance in the three-dimensional protein structure between the two tone-generating block pieces. Specifically, the harmonic's intensity drops, roughly, with the sixth power of the distance d between the two methyls, i.e., as $1/d^6$, so that, effectively, there is a threshold distance, namely 10 Å, beyond which the possibility of the harmonic between two tones being "audible" can be safely ruled out as illustrated in FIG. 3. Moreover, due to "obstructions," not all potentially audible harmonics end up being present (heard) in experimental NOE data. In principle, given the three-dimensional structure of the polymer one could try to determine which ones will be heard and which ones will not. But the complexity of the underlying physical process vastly exceeds the capacity to perform such computations. All one can say with confidence is that the fraction of observed harmonics is typically 30-40% of the potential ones and even that can only be asserted in a highly statistical sense, e.g., as an aggregate over many different proteins, observability correlates with distance, e.g., harmonics corresponding to pairs of methyls closer together are more likely to be observed.

So, overall, when NOE data is used, the primary (loud) tone emitted by each sensor (methyl) is detected. However, it is not known to which block piece it corresponds. That is the problem to be solved. The harmonics are detected at varying intensities. With each such harmonic a small number of candidate-pairs of primary tones can be associated, such that the pair actually generating the harmonic is one of the candidates. This, in turn, implies that the two associated methyls of (at least) one of the candidate pairs, are close in the three-dimensional structure. The greater the harmonic's intensity, the smaller the distance. In each target protein there is a collection of "geminal pairs" of methyls (e.g., $^{13}C^\delta H_3$ $^{12}C^\delta D_3$ labeled leucines and $^{13}C^\gamma H_3$, $^{12}C^\gamma D_3$ labeled valines) that can be determined from the three-dimensional structure of the target protein. Each pair of which generates a harmonic of far greater intensity than those coming from non-geminal pairs. These harmonics are useful "intensity yardsticks" when trying to correlate the intensity of "non-geminal" pairs to geometric distance.

To consider this assignment problem further, a completely arbitrary mapping of the methyl tones to the tone-producing block pieces can be drawn without looking at the data at all. With overwhelming probability, there would be at least one harmonic in the NOE data whose two methyls were mapped "too far from one another for their harmonic to be audible," thus refuting the (randomly chosen) mapping. Unfortunately, there are too many possible mappings to consider individually. Specifically, if one were to map 100 methyls, for a target protein of modest size, the number of possible mappings is $100.99 \ldots 2.1 \approx 10^{158}$. By way of comparison, the number of elementary particles in the universe is estimated to be $10^{86}$. This astronomical number is too large for conventional data processing techniques.

How to Address the Shortcomings of the Assignment Problem.

In conventional practice, a researcher would need to spend three to six months solving the methyl assignment problem through trial and error, with the help of a modicum of additional chemistry. This is a cost of approximately $12,500 if post-doctoral research time at nominal post-doctoral salaries were utilized. Moreover, since there are no guarantees for the correctness of the derived map, the researcher often then needs to also validate it independently using conventional approaches. The three to six-month cost in time greatly subsumes the monetary cost. This is because it completely prohibits a lab from pursuing more than a handful of different target proteins at a time. Moreover, each such pursuit represents a very strong commitment of resources, discouraging "exploration" of potentially interesting molecules as therapeutic targets for human diseases. As such, the study of larger target proteins by NMR, in spite of being an extremely powerful tool, remains prohibitively out of reach for the average biomedical research lab.

If the methyl assignment problem from NOE data could be solved quickly, it would greatly benefit NMR of large proteins: a full NOE dataset could be recorded in a single NMR experiment, from a single target protein sample in 1-2 days. To aid with methyl assignment, an additional, non-NOE-based experiment could be done to yield the amino acid type of each methyl emitting tone and the geminal methyl pairs (using a differently prepared sample, also in one to two days). This represents significant progress over current approaches which require several months in the case of the through-the bond transfer approach and several weeks and hundreds of NMR experiments/samples in the case of the one-at-a-time isotopic labeling approach described above. The gains in time and resources could then be utilized to study several target proteins in parallel, with each one being a potential therapeutic target of high value.

Thus, what is needed in the art are improved methods for obtaining assignment information for target proteins that have been isotopically labeled.

SUMMARY

The present disclosure addresses the deficiencies described above. In the present disclosure, computing systems and methods for characterizing a protein are provided. Each residue in a subset of residues of the protein is a member of an enumerated amino acid type set and is represented by a vertex in an original graph G that is formed from an atomic model of the protein. In some embodiments, each edge in G is assigned a first edge type when it represents a geminal pair of methyls within a threshold distance of each other in the atomic model and is otherwise assigned a second edge type. Nuclear magnetic resonance data of the protein acquired with a subset of the residues of the protein labeled is used to form an observed graph H. In some embodiments, each edge in H is a first edge type when it represents NMR data satisfying an intensity or volume threshold and is otherwise a second edge type. Each vertex in H is assigned one or more amino types in the enumerated amino acid type set using amino acid type assignments made by the NMR data. Each vertex in H represents a different residue of the protein. A plurality of placements of H onto G, is formed. Each such placement includes a plurality of mappings, each assigning a vertex in G to a vertex in H subject to the constraints that (i) when a vertex v in H maps to a vertex w in G, the amino acid type assigned w is in the one or more amino acid types assigned v and (ii) for edge {a, b} between vertices a and b in H, when vertex a maps to vertex v and vertex b maps vertex w in G, there exists an edge {v, w} between v and w in G and with the same edge type as {a, b}. For each vertex in H, a number of different mappings for the vertex into G is determined by polling the plurality of placements as a constraint satisfaction problem. A vertex in H is uniquely assigned to a vertex in G when only a single unique assignment is made through such evaluation.

Another aspect of the present disclosure provides a computing system for characterizing a target protein or an interaction of the target protein with an entity. The computing system 100 comprises one or more processors and memory storing one or more programs for execution by the one or more processors. The one or more programs singularly or collectively executing a method. In the method, a first data construct is formed comprising an original graph G from an atomic model of the target protein. The original graph G comprises a first plurality of vertices and a first plurality of edges. Each residue in a first plurality of residues of the target protein is a member of an enumerated amino acid type set (e.g. ILE, VAL, LEU, ALA, MET, THR). Each respective vertex in G represents a different residue in the first plurality of residues and is further assigned the amino acid type, in the enumerated amino acid type set, of the different residue. Each respective edge in G uniquely represents a pair of vertices in G that are within a threshold distance of each other in the atomic model.

In some embodiments, each respective edge in the original graph G is assigned a first edge type when the pair of vertices represented by the respective edge are for a geminal pair of methyls in the atomic model and is assigned a second edge type otherwise.

In some embodiments, the enumerated amino acid set consists of two or more of the group consisting of alanine, valine, isoleucine, leucine, methionine, and threonine. In some embodiments, the enumerated amino acid set consists of three or more of the group consisting of alanine, valine, isoleucine, leucine, methionine, and threonine. In some embodiments, the enumerated amino acid set consists of four or more of the group consisting of alanine, valine, isoleucine, leucine, methionine, and threonine.

In some embodiments, the target protein comprises 50, 100, 150, 200, 250, 300, 350, or 400 amino acid residues.

In some embodiments, the atomic model of the target protein includes spectroscopically determined coordinates for each atom of all or a portion of the target protein. In some embodiments, the coordinates for each atom of the target protein or the portion of the target protein are determined by nuclear magnetic resonance, x-ray crystallography, or electron microscopy. In some embodiments, the atomic model of all or a portion of the target protein is determined from homology modeling of spectroscopically determined atomic coordinates of all or a portion of one or more second proteins other than the target protein.

In some embodiments, the target protein comprises at least one, two, three, four, five, six, seven, eight, nine, ten, eleven, twelve, thirteen, fourteen, fifteen, sixteen or seventeen different amino acid types that are not in the enumerated amino acid type set in addition to amino acid types that are in the enumerated amino acid type set.

In accordance with the disclosed methods, a primary nuclear Overhauser enhancement (NOE) dataset of a sample comprising the target protein in perdeuterated form in which a second plurality of residues of the target protein have been isotopically labeled in the sample of the target protein is taken. Each residue in the second plurality of residues is a member of the enumerated amino acid type set.

In some embodiments, the enumerated amino acid type set comprises isoleucine, leucine, valine, serine, alanine, and methionine. In some such embodiments, each isoleucine residue in the second plurality of residues is $^{13}C\delta H_3$ labeled, each leucine residue in the second plurality of residues is ($^{13}C\delta H_3$, $^{12}C\delta D_3$) labeled, each valine residue in the second plurality of residues is ($^{13}C\delta H_3$, $^{12}C\delta D_3$) labeled, each serine residue in the second plurality of residues is ($^{2}H_2$, $^{13}CH_3$) labeled, each alanine residue in the second plurality of residues is ($^{13}CH_3$) labeled, and each methionine residue in the second plurality of residues is ($^{13}CH_3$) labeled.

In some embodiments, the sample of the target protein is fully deuterated other than for the isotopic label in each residue in the second plurality of residues.

In some embodiments, each respective residue in the second plurality of residues is $^{13}C$ isotopically labeled at a single methyl in the side chain of the respective residue.

In some embodiments the NOE primary dataset is acquired using a methyl selective three dimensional CCH NOESY pulse sequence. In some embodiments, the primary NOE dataset is acquired using a pulse sequence that facilitates evaluation of the primary NOE dataset using (i) a two-dimensional plane that correlates a first $^{13}C$ carbon to a proton attached to the first $^{13}C$ carbon in the target protein (e.g., a $^{13}C$ carbon to one of its covalently bound H) and (ii) a third dimension that correlates the first $^{13}C$ carbon with a second $^{13}C$ carbon in the target protein (e.g., a first $^{13}C$ isotopically labeled carbon in a methyl of a first residue to a second $^{13}C$ isotopically labeled carbon in a methyl of a second residue in the target protein) the through space.

In the disclosed methods, a plurality of cross peaks is identified in the primary NOE dataset 22. Each respective cross peak 62 in the primary NOE dataset is generated by NOE interaction between an isotopic label in a different first residue and an isotopic label in a different second residue in the second plurality of residues. In some embodiments, the plurality of cross peaks comprises 10, 20, 30, 40, 50, 60, 70, 80, 90, 100, 110, 120, 130, 140, or 150 cross peaks. In some embodiments each residue in the second plurality of residues is $^{13}C$ isotopically labeled at a single methyl in the side chain of the residue. In some such embodiments, the identifying comprises (i) identifying a plurality of C, C, H triplets in the primary NOE dataset. Each triplet is formed from (a) an interaction between a first $^{13}C$ labeled carbon in a methyl in a side chain of a first residue and a proton covalently bound to the first $^{13}C$ labeled carbon and (b) an interaction between the first $^{13}C$ labeled carbon and a second $^{13}C$ labeled carbon in a methyl in a side chain of a second residue. The triplets are symmetry filtered thereby identifying a reduced set of triplets. The triplets in the reduced set are clustered using the second and third coordinates of each triplet thereby forming a plurality of clusters of triplets. Each respective cluster of triplets is deemed to be a cross peak in the plurality of cross peaks.

In the disclosed methods a second data construct is formed from the plurality of cross peaks. The second data construct comprises an observed graph H. The observed graph H comprises a second plurality of vertices and a second plurality of edges. Each respective vertex in the second plurality of vertices represents a different residue in the second plurality of residues. Each respective edge in the second plurality of edges represents a corresponding cross peak in the plurality of cross peaks. Each respective vertex is assigned one or more amino acid types in the enumerated amino acid type set using amino acid type assignments made by the primary NOE dataset or one or more secondary NMR datasets taken of the target protein.

In some embodiments, a respective edge in the second plurality of edges is assigned a first edge type when the cross peak in the plurality of cross peaks corresponding to the respective edge satisfies an intensity threshold and is otherwise assigned the second edge type.

In some embodiments, the second plurality of vertices of the observed graph H is less than the first plurality of vertices of the original graph G.

In some embodiments, at least one vertex in the second plurality of vertices of the observed graph H is assigned two or more amino acid types in the enumerated amino acid type set using amino acid type assignments made by the primary NOE dataset or one or more secondary NMR datasets taken of the target protein.

In the disclosed methods a plurality of placements of the observed graph H onto the original graph G is created. Each respective placement in the plurality of placements (i) includes a plurality of mappings and (ii) maps all the vertices of the observed graph H onto different vertices in the original graph G. Each mapping in the plurality of mappings assigns a vertex in the observed graph H to a vertex in the original graph G. Each respective placement in the plurality of placements is subject to a set of constraints including the constraint that, when a vertex v in the observed graph H is mapped to a vertex w in the original graph G, the amino acid type assigned vertex w in the original graph G is in the one or more amino acid types assigned vertex v. The set of constraints further requires that, for an observed edge {a, b} between a vertex a and a vertex b in the observed graph H, when vertex a is mapped to a vertex v and vertex b is mapped to a vertex w in the original graph G, there exists an edge {v, w} between the vertex v and the vertex w in the original graph G.

In some embodiments, the set of constraints further requires that, when the observed edge {a, b} in the observed graph His assigned the first edge type, the edge {v, w} in the original graph G is also assigned the first edge type.

In some embodiments, the threshold distance used for identifying edges between vertices in the original graph G is initially 10 Å. In some embodiments, the threshold distance used for identifying edges between vertices in the original graph G is initially 6.5 Å, 7.0 Å, 7.5 Å, 8.0 Å, 8.5 Å, 9.0 Å, 9.5 Å, or 10 Å.

In some embodiments, the threshold distance is increased from the initial distance to a larger distance when the creating fails to create a first threshold number placements for the plurality of placements. In such embodiments, the threshold distance is decreased from the initial distance to a smaller distance when the creating creates more than a second threshold number placements for the plurality of placements.

In the disclosed methods, each set in a plurality of sets is initialized. Each set in the plurality of sets representing a different vertex in the observed graph H. Then a determination is made, for each respective set in the plurality of sets, of a number of different mappings for the vertex i represented by the respective set in the observed graph H into the original graph G by polling the plurality of placements as a constraint satisfaction problem in which, for each respective possible assignment of the vertex i into the original graph G. When a determination is made that there exists a mapping in the plurality of mappings that includes the respective assignment, the respective set is advanced, and is not advanced otherwise.

A vertex in the observed graph H is deemed to be uniquely assigned to a vertex in the original graph G when the set for the respective vertex includes a single unique assignment upon completion of the polling of the plurality of placements as a constraint satisfaction problem. In some embodiments, the method uniquely assigns at least forty, fifty, sixty, seventy, or eighty percent of the vertices in the observed graph H to the original graph G. In some embodiments, the entity is a second protein that binds with target protein and the deeming identifies a portion of a surface of the target protein that is bound by the second protein. In some embodiments, the entity is an inhibitor that binds with target protein and the deeming identifies a portion of a surface of the target protein that is bound by the inhibitor. In some such embodiments, the inhibitor has a molecular weight of less than 5000 Daltons. In some such embodiments, the inhibitor is a chemical compound that satisfies at least three, at least four or all five of the Lipinski rule of five criterion.

In some embodiments, the unique assignment of a first vertex in the observed graph H to the original graph G is used to assign a first peak in the NOE dataset to a first residue in the atomic model and a second peak in the NOE dataset to a second residue in the atomic model. The first peak and the second peak are not within the plurality of cross peaks and a label of the first residue and a label of the second residue are deemed to create the cross peak in the plurality of cross peaks represented by the first vertex.

BRIEF DESCRIPTION OF THE DRAWINGS

For a better understanding of the aforementioned implementations of the subject systems and methods as well as additional implementations thereof, reference should be made to the Description of Implementations below, in conjunction with the following drawings in which like reference numerals refer to corresponding parts throughout the figures.

FIGS. 1A, 1B, 1C, 1D, and 1E illustrate a computer system for automated assignment of labeled groups in selectively isotope-labelled target proteins using a predetermined three-dimensional structure of the target protein and nuclear magnetic resonance (NMR) data of the target protein in accordance with some embodiments.

FIGS. 2A, 2B, 2C, 2D, 2E, and 2F illustrate methods for automated assignment of labeled groups in selectively isotope-labelled target proteins using a predetermined three-dimensional structure of the polymer and NMR data of the target protein. In these figures, elements in dashed boxes are optional.

FIG. 3 is a plot of $1/d^6$, for $d \in [3, 12]$, where it is seen that $d=10$ is practically the same as $d=\infty$, in accordance with the prior art.

FIG. 6 illustrates the number of valid placements of graph H onto graph G in accordance with some embodiments.

FIG. 7 illustrates a plurality of valid placements when there are bichromatic vertices in accordance with some embodiments.

Like reference numerals refer to corresponding parts throughout the several views of the drawings.

Figure 1A:
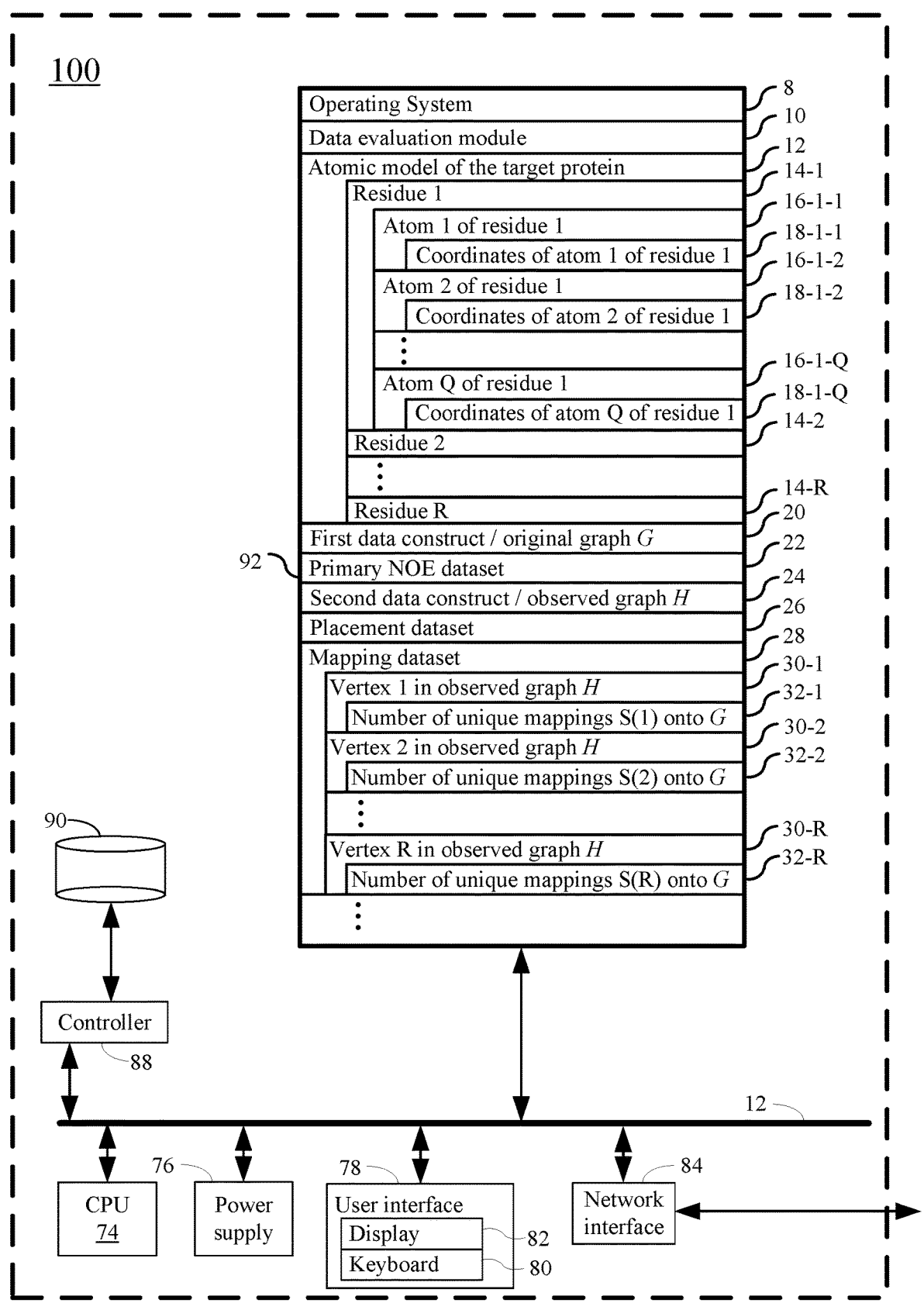

Reference will now be made in detail to implementations, examples of which are illustrated in the accompanying drawings. In the following detailed description of implementations, numerous specific details are set forth in order to provide a thorough understanding of the present invention. However, it will be apparent to one of ordinary skill in the art that the present invention may be practiced without these specific details.

DETAILED DESCRIPTION

The present disclosure addresses the methyl assignment problem using computational techniques that, in some instances, take less than five minutes to run on a computer system. The disclosed systems and methods work both quickly and accurately for real-life NOE data sets of large proteins. In particular, in some embodiments, the disclosed systems and methods reaches the information theoretic limit. That is, for any NOE NMR data set, the disclosed systems and methods either solves the methyl assignment problem, or proves, in a strict mathematical sense, that the given NOE data is insufficient to uniquely determine the methyl map, in the same way that a shadow of an object can be sufficient or insufficient for reconstructing its three-dimensional form. In either case, the disclosed systems and methods maximally restricts the set of possible maps.

In the disclosed methods, a threshold distance, such as $d=10$ Å, is selected and the assumption is made that the harmonic of a pair of methyls at a distance greater than this threshold distance d in the target protein is not detected in a NOE NMR dataset. The greater d is set, the safer the assumption. With this in mind for a fixed value of the predetermined threshold d, given the three-dimensional structure of the atomic model of the target protein, it possible to determine the set of all potentially observable harmonics, e.g., the set of all pairs of isotopically labeled methyls within the predetermined distance d to each other in the atomic model of the target protein. Moreover, it is possible to determine the "geminal pairs" of methyls, that is, the methyls that are on the same side chain of a given amino acid in the target protein (e.g., leucine, valine, isoleucine). When the NOE data is acquired of the target protein, a map (methyl assignment) is sought that is consistent with this assumption. If none exists, the assumption is deemed incorrect and the predetermined threshold d is increased. If many exist, the value of the predetermined distance d is decreased. Through such a search, the smallest value $d_0$ is identified for which at least one valid map exists. To be conservative, in some embodiments, it is assumed that all harmonics in the NOE data come from pairs within $d_{0+s}$, where s is a safety factor. The greater the safety factor is, the safer the assumption.

The disclosed systems and methods advance the art in at least two ways. First, the art is advanced by formulating the problem in a manner that is amendable to efficient computation. This formulation is very different from a mathematically equivalent formulation. Knowing what is computationally tractable is an art that requires significant insights into computational complexity. Put differently, the conventional methods that have been applied to the methyl assignment problem fail to take into account the relative strengths and weaknesses of computational techniques. Having formulated the problem in a manner that is computationally tractable, the second contribution of the disclosed systems and methods is to: (i) identify computer algorithms that are well-suited to the task at hand, and (ii) improve them in order to solve the methyl assignment problem.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

FIG. 1 illustrates a computer system 100 for characterizing a target protein or the interaction of the target protein with another entity such as a protein inhibitor.

Referring to FIG. 1, in typical embodiments, analysis computer system 100 comprises one or more computers. For purposes of illustration in FIG. 1, the analysis computer system 100 is represented as a single computer that includes all of the functionality of the disclosed analysis computer system 100. However, the disclosure is not so limited. The functionality of the analysis computer system 100 may be spread across any number of networked computers and/or reside on each of several networked computers. One of skill in the art will appreciate that a wide array of different computer topologies are possible for the analysis computer system 100 and all such topologies are within the scope of the present disclosure.

Turning to FIG. 1 with the foregoing in mind, an analysis computer system 100 comprises one or more processing units (CPU's) 74, a network or other communications interface 84, a user interface 78 (e.g., including a display 82 and keyboard 80 or other form of input device) a memory 92 (e.g., random access memory), one or more magnetic disk storage and/or persistent devices 90 optionally accessed by one or more controllers 88, one or more communication busses 12 for interconnecting the aforementioned components, and a power supply 76 for powering the aforementioned components. Data in memory 92 can be seamlessly shared with non-volatile memory 90 using known computing techniques such as caching. Memory 92 and/or memory 90 can include mass storage that is remotely located with respect to the central processing unit(s) 74. In other words, some data stored in memory 92 and/or memory 90 may in fact be hosted on computers that are external to analysis computer system 100 but that can be electronically accessed by the analysis computer system over an Internet, intranet, or other form of network or electronic cable using network interface 84.

The memory 92 of analysis computer system 100 stores:
an operating system 8 that includes procedures for handling various basic system services;
a data evaluation module 10 for characterizing a target protein or an interaction of the target protein with an entity;
an atomic model 12 of the target protein that includes, in some embodiments, for each residue 14 represented by the atomic model of the target protein, atomic coordinates of each atom 18 of the residue;
a first data construct comprising an original graph G 20 for the target protein that is formed based on the atomic model;
at least one Nuclear Overhauser Enhancement (NOE) dataset 22 taken of the protein 22;
a second data construct 24 comprising an observed graph H 24 for the target protein that is formed based on the NOE dataset 22;
a placement dataset 26 comprising a listing of valid placements of the observed graph H 24 onto the original graph G 20; and
a mapping dataset 28 that comprises, for each vertex 30 in the observed graph H, the number of unique mappings 32 of the vertex 30 onto the original graph H upon completion of an evaluation of the placement dataset 26 as a constraint satisfaction problem.

FIG. 1B provides more details of a first data construct comprising an original graph H 20 in accordance with some embodiments of the present disclosure. The original graph G represents a subset of the residues 14 of the protein 12. Each residue in the subset of residues represented by the original graph G is a member of an enumerated amino acid type set (e.g., the set {alanine, valine, isoleucine, leucine, methionine, and threonine}). The original graph G comprises a plurality of vertices 34 and a plurality of edges 42. In some embodiments, each respective vertex is assigned a vertex identifier 34 that uniquely identifies the vertex within the graph. Each respective vertex 34 represents a particular residue in the subset residues represented by the graph, which is termed a residue assignment 38 in the present disclosure. Each respective vertex 34 is thus associated with an amino acid type assignment 40 based on the residue assignment of the particular vertex. For instance, if the residue assignment of a respective vertex of the graph G is isoleucine 103 of the protein, then the amino acid type assignment 40 for the respective vertex is "isoleucine."

In some embodiments, each respective edge 42 in the graph G is assigned a unique edge identifier 44. Each respective edge 42 in the original graph G uniquely represents a pair of vertices {48, 50} in the graph from the set of vertices 34 of the graph G that are within a threshold distance of each other in the atomic model 12 of the target protein. In some embodiments, each respective edge 42 in the original graph G is further assigned an edge type 46. An edge 42 is assigned a first edge type when the pair of vertices {48, 50} represented by the respective edge 42 are for a geminal pair of methyls in the atomic model. An edge 42 is assigned a second edge type when the pair of vertices {48, 50} represented by the respective edge 42 are not for a geminal pair of methyls in the atomic model.

FIG. 1C provides more details of a Nuclear Overhauser Enhancement (NOE) dataset 22 in accordance with some embodiments of the present disclosure. The NOE dataset 22 comprises a plurality of diagonal peaks 52. In some embodiments, each such diagonal peak 52 is assigned a unique diagonal peak identifier 54. In some embodiments, each respective diagonal peak includes a residue assignment 56 to a residue in the target protein. In typical embodiments, the residue assignment 56 for a given diagonal peak 52 is not initially known. In some embodiments the NOE dataset 22 is a two-dimensional dataset and each diagonal peak 52 is characterized by a first part-per-million (PPM) value 58 in a first dimension (corresponding to a first pulse sequence type) and a second PPM value 60 in a second dimension (corresponding to a second pulse sequence type).

The NOE dataset further comprises a plurality of cross peaks 62. In some embodiments, each respective cross peak 62 in the NOE dataset is generated by an interaction between a pair of labeled residues in the protein. In some embodiments, each cross peak 62 is assigned a unique cross peak identifier 63. In some embodiments the NOE dataset 22 is a two-dimensional dataset and each cross peak 62 is characterized by a first part-per-million (PPM) value 64 in a first dimension and a second PPM value 66 in a second dimension. In some embodiments, each respective cross peak 62 includes a volume or intensity value 68 that quantifies an observed strength of the cross peak. Each cross peak 62 is formed from the interaction of a label (e.g., $^{13}C$) associated with a first diagonal peak 52 and a second diagonal peak 52 in the dataset. However, typically, at least initially, the identity of the labels within the target protein that generate the cross peak are not known. In some embodiments, only one of the diagonal peaks that generate a cross peak is associated with an atom that is isotopically labeled. In some embodiments, both of the diagonal peaks that generate a cross peak are associated with atoms that are isotopically labeled. In some embodiments, each of the cross peaks are generated from diagonal peaks that are both associated with atoms that are isotopically labeled and some of the cross peaks are generated from diagonal peaks where only a single one of the diagonal peaks is associated with an atom that is isotopically labeled. In some embodiments, when the identity of these labels is determined, they are indicated as identities 70 and 72, respectively.

FIG. 1D provides more details of a second data construct/observed graph H 24 in accordance with some embodiments of the present disclosure. The observed graph H is formed, at least in part, using the characteristics of the plurality of cross peaks 62 in the NOE dataset 22. The observed graph H comprises a plurality of vertices 96 and a plurality of edges 106. In some embodiments, each respective vertex 96 in the observed graph H 24 is assigned a different vertex identifier 98. Each vertex 98 represents a different label in the target protein. Moreover, in typical embodiments, each residue in the target protein is labeled with, at most, a single label. Thus, in such embodiments, each vertex 98 represents a different residue in the protein. In typical embodiments, not all the residues of a protein are labeled and thus there does not exist a vertex for all the residues in the target protein. At least initially, the identity of the residues in the target protein that a given vertex 98 represents is not known. The NOE data provides some insight as to the possible residues a given vertex 96 may represent. For instance, the $^{13}C$ labeled isoleucines in the target protein will resonate in a manner that is distinguishable from the $^{13}C$ labeled valines in a protein. Using such information, possible residue assignments 100 for each vertex 96 are made. Each such possible residue assignment 100 includes the amino acid type 102 of the assignment.

In typical embodiments, each respective edge 106 in the observed graph H is assigned an edge identifier 108. In typical embodiments, each respective edge 106 in the observed graph H represents a corresponding cross peak 62 in the NOE dataset 22. In typical embodiments, a respective edge 106 in the observed graph H is assigned a first edge type when the corresponding cross peak satisfies an intensity threshold and is otherwise assigned a second edge type. The edge type (first edge type or second edge type) of a given edge 106 in the observed graph H is stored as edge type 112.

Figure 1E:
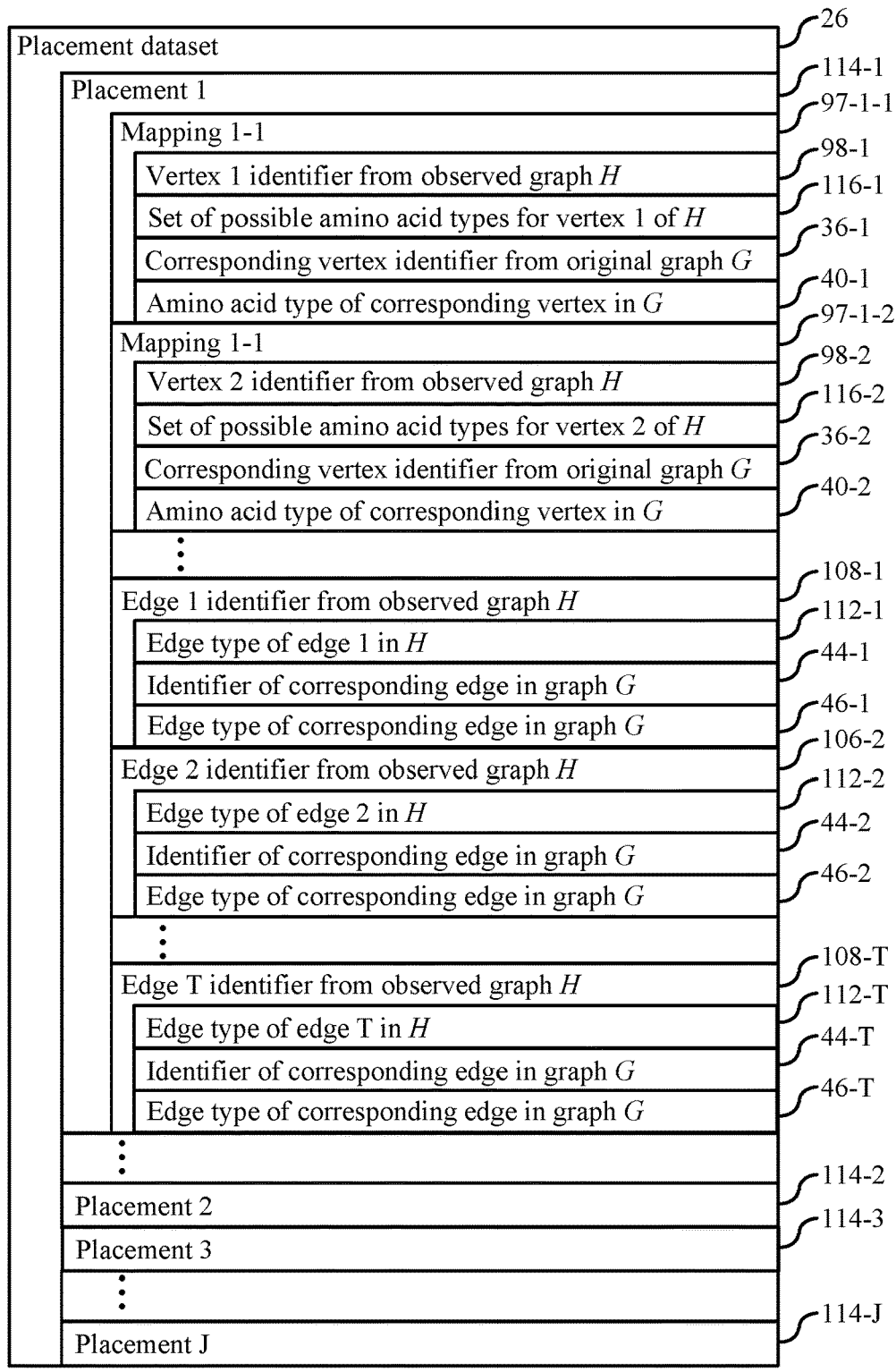

FIG. 1E provides more details of a placement dataset 26 in accordance with some embodiments of the present disclosure. The placement dataset 26 comprises a plurality of placements of the observed graph H onto the original graph G. Each respective placement 114 includes a plurality of mappings. Each respective mapping 97 in a given plurality of mappings assigns a vertex identifier 98 in the observed graph H to a corresponding vertex 36 in the original graph G. In typical embodiments, each respective placement 114 in the plurality of placements is subject to a set of constraints. One such constraint in the set of constraints is that, when a vertex v in the observed graph H is mapped to a vertex w in the original graph G, the amino acid type assigned vertex w in the original graph G is in the one or more amino acid types assigned vertex v. Thus, for a given mapping 97, the amino acid type assignment 40 of the corresponding vertex 36 in G must be within the set of possible amino acid types 116 for the subject vertex 98 in graph H in such embodiments. Another such constraint is that, for an observed edge {a, b} 106 between a vertex a and a vertex b in the observed graph H, when vertex a is mapped to a vertex v and vertex b is mapped to a vertex w in the original graph G, there exists an edge {v, w} between the vertex v and the vertex w in the original graph G.

In some implementations, one or more of the above identified data elements or modules of the analysis computer system 100 are stored in one or more of the previously disclosed memory devices, and correspond to a set of instructions for performing a function described above. The above identified data, modules or programs (e.g., sets of instructions) need not be implemented as separate software programs, procedures or modules, and thus various subsets of these modules may be combined or otherwise re-arranged in various implementations. In some implementations, the memory 92 and/or 90 optionally stores a subset of the modules and data structures identified above. Furthermore, in some embodiments the memory 92 and/or 90 stores additional modules and data structures not described above.

Now that a system for characterizing a target protein or the interaction of the target protein with an entity has been disclosed, methods for performing this characterization are discussed below with reference to FIG. 2.

Referring to block 202 of FIG. 2A, a computing system 100 for characterizing a target protein or an interaction of the target protein with an entity, as described above in conjunction with FIGS. 1A, 1B, 1C, 1D, and 1E, is provided. The computing system 100 comprises one or more processors 74 and memory 90/92 storing one or more programs for execution by the one or more processors. The one or more programs singularly or collectively execute the methods detailed in the present disclosure.

The disclosed systems and methods address the problem of characterizing the target protein or an interaction of the target protein with an entity using NOE NMR data in which some or all of the methyls in side chains of the target protein have been isotopically labeled. As noted in the background section above, this reduces the problem to a methyl assignment problem. Once the peaks in a NOE NMR data that originate from isotopically labeled methyls, or the interaction of such methyls with each other, have been assigned, it is possible to conduct experiments with the target protein both in the presence and absence of an entity. By correlating shifts in certain of such peaks with the presence or absence of the entity in the NOE NMR sample, it is possible to identify which methyls are affected by the entity and thus where on the surface of target protein the entity binds.

In the present disclosure, the methyl assignment problem is formulated using some elements of graph theory. Thus, returning to the analogy in which each of the naturally occurring amino acids is a different block type, the graph theory approach of the present disclosure begins by enhancing all the block pieces in four bins with sensors. That is, four different types of block pieces have been isotopically labeled. In practice, any number between one different block type up to six different block types can be replaced (or more if non-naturally occurring labeled amino acids are used), but to facilitate discussion, the example of four different types of block pieces is discussed. If the total number of block pieces in the target protein from these four bins is n, then n dots can be drawn in random locations on paper. Each dot is colored with one of four colors, so as to designate the bin (amino acid) from which it came.

Recall that in each block piece for which a dot is drawn, there is a methyl (sensor). So, for every one of the $$\binom{(n)}{2} = n(n-1)/2$$

pairs of methyls the distance in the three-dimensional model of the target protein is measured.

In some embodiments, if the two methyls are connected through a chemical bond in the three-dimensional structure of the target protein (the atomic model of the target protein 12) (also called a "germinal pair" in chemistry), their dots are connected with a red line. In other words, the two vertices 34 represented by these methyls are connected by an edge 42 having a first edge type 46. Such pairs are so close in space (e.g., 3.5 Å) that they should generate a very intense harmonic in the NOE data (e.g., geminal methyls in valines, leucines and isoleucines). If the two methyls do not form a geminal pair but their distance is at most d, then their two dots are connected with a blue line. In other words, the two vertices 34 represented by these methyls are connected by an edge 42 having a second edge type 46. In all other cases, do nothing. That is, no other edges, and no other edge types are included in the graph. This drawing can be termed a graph, consisting of vertices (dots) and edges (connections). In particular, the graph G=G(V, E) created in this manner is termed the original graph. In some embodiments, the edges are not assigned edge types and, rather, edges 42 are created when the methyl pair they represent in the atomic model 12 is at most d but such edges are not assigned an edge type based on whether or not they represent a geminal pair of methyls.

Referring to block 210 of FIG. 2A, in some embodiments the target protein comprises 50, 100, 150, 200, 250, 300, 350, or 400 amino acid residues. As used herein, the term "protein" means two or more amino acids or residues linked by a peptide bond. The terms "polypeptide" and "protein" are used interchangeably and include oligopeptides and peptides. In some embodiment, an "amino acid," or "residue" refers to any of the twenty standard structural units of proteins as known in the art, which include imino acids, such as proline and hydroxyproline, and isomers thereof. The designation of an amino acid isomer may include D, L, R and S. The definition of amino acid includes nonnatural amino acids. Thus, selenocysteine, pyrrolysine, lanthionine, 2-aminoisobutyric acid, gamma-aminobutyric acid, dehydroalanine, ornithine, citrulline and homocysteine are all considered amino acids that can be used in the target proteins addressed by the systems and methods of the present disclosure. Other variants or analogs of the amino acids are known in the art. Thus, a target protein may include synthetic peptidomimetic structures such as peptoids. See Simon et al., 1992, Proceedings of the National Academy of Sciences USA, 89, 9367, which is hereby incorporated by reference herein in its entirety. See also Chin et al., 2003, Science 301, 964; and Chin et al., 2003, Chemistry & Biology 10, 511, each of which is incorporated by reference herein in its entirety.

A target protein may also have any number of posttranslational modifications. Thus, the target proteins addressed by the present disclosure includes those that are modified by acylation, alkylation, amidation, biotinylation, formylation, γ-carboxylation, glutamylation, glycosylation, glycylation, hydroxylation, iodination, isoprenylation, lipoylation, cofactor addition (for example, of a heme, flavin, metal, etc.), addition of nucleosides and their derivatives, oxidation, reduction, pegylation, phosphatidylinositol addition, phosphopantetheinylation, phosphorylation, pyroglutamate formation, racemization, addition of amino acids by tRNA (for example, arginylation), sulfation, selenoylation, ISGylation, SUMOylation, ubiquitination, chemical modifications (for example, citrullination and deamidation), and treatment with other enzymes (for example, proteases, phosphatases and kinases). Other types of posttranslational modifications are known in the art and are also within the scope of the systems and methods of the present disclosure.

In some embodiments, the target protein has a molecular weight of 10 kDa or more, 15 kDa or more, 20 kDa or more, 25 kDa or more, 30 kDa or more, 35 kDa or more, 40 kDa or more, 45 kDa or more, 50 kDa or more, 55 kDa or more, 60 kDa or more, 65 kDa or more, 70 kDa or more, 75 kDa or more, or 80 kDa or more.

In some embodiments, the different types of amino acids that are $^{13}C$ isotopically methyl labeled in the target protein constitutes the enumerated set of amino acids. For instance, if isoleucine and leucine are $^{13}C$ isotopically methyl labeled in a target protein, the enumerated set consists of isoleucine and leucine. In some embodiments, the percentage of amino acid residues that are in the enumerated set of the target protein is between 5 and 10 percent of the residues in the target protein. In other words, using the example where the enumerated set consists of isoleucine and leucine, and collectively between 5 and 10 percent of the residues in the target protein are either isoleucine or leucine, the enumerated set of the target protein is between 5 and 10 percent of the residues in the target protein. In some embodiments the enumerated set of the target protein is between 10 and 15 percent of the residues in the target protein, between 15 and 20 percent of the residues in the target protein, between 20 and 25 percent of the residues in the target protein, between 25 and 30 percent of the residues in the target protein, between 30 and 35 percent of the residues in the target protein, between 35 and 40 percent of the residues in the target protein, between 40 and 45 percent of the residues in the target protein, more than 45 percent of the residues in the target protein, more than 80 percent of the residues in the target protein, or less than 95 percent of the residues in the target protein.

In some embodiments, the graph discussed above is formulated as a first data construct that comprises an original graph G 20. As discussed above, an atomic model 12 of the target protein is used to form the original graph G. The original graph G comprises a first plurality of vertices 34 and a first plurality of edges 42. As discussed above in the block type analogy, each residue in a first plurality of residues of the target protein is represented by the original graph G. In typical embodiments, each residue is selectively $^{13}C$ isotopically labeled at a single methyl on its side chain. In typical embodiments, in the case where an amino acid includes two side chain methyls (e.g., valine, leucine, isoleucine) only one of the methyls is $^{13}C$ isotopically labeled although the $^{13}C$ labeling of both methyls is within the scope of the present disclosure. Methods for forming target proteins that are $^{13}C$ isotopically methyl labeled are known. See, for example, Monneau et al., 2016, "Exploiting E. coli auxotrophs for leucine, valine, and threonine specific methyl labeling of large proteins for NMR applications," J. Biomol. NMR 65(2), pp. 99-108, which is hereby incorporated by reference. The present disclosure further contemplates the use of non-naturally occurring amino acids in the target protein that include one or more $^{13}C$ isotopically labeled methyl group in their side chains.

In any event, each amino acid residue represented by the original graph G 20 is a member of an enumerated amino acid type set. In other words, the types of amino acid residues that have had a side chain $^{13}$C methyl group labeled is predetermined and constitutes the enumerated amino acid type set. In typical embodiments the enumerated amino acid type set consists of the six naturally occurring amino acids that contain at least one methyl group in their side chain (e.g. ILE, VAL, LEU, ALA, MET, THR), or a subset thereof. That is, the residues that are isotopically $^{13}$C methyl labeled, and thus represented by vertices 34 in the original graph 20, are in the set of naturally occurring amino acids that have one or methyl groups in their side chains in such embodiments. In some embodiments, only a subset of the naturally occurring amino acids that include a methyl group in their side chain are isotopically $^{13}$C methyl labeled and thus represented by vertices 34 in the original graph 20. For instance, in some embodiments, only a methyl of a side chain of each isoleucine and valine in the target protein is isotopically $^{13}$C methyl labeled and thus represented by vertices 34 in the original graph 20. In such an example, the enumerated amino acid type set consist of (isoleucine, valine). As another example, in some embodiments, only a methyl of a side chain of each alanine and methionine in the target protein is isotopically $^{13}$C methyl labeled and thus represented by vertices 34 in the original graph 20. In such an example, the enumerated amino acid type set consists of (alanine, methionine). In typical embodiments, when a given amino acid type is isotopically $^{13}$C methyl labeled, each instance of the given amino acid type in the target protein is isotopically $^{13}$C methyl labeled. Thus, if there are 23 valines in the target protein, each one of the valines is isotopically $^{13}$C methyl labeled and each one of the 23 valines is uniquely represented by a different vertex 34 in the original graph 20.

Referring to block 204 of FIG. 2A, in some embodiments, the enumerated amino acid set consists of two or more of the group consisting of alanine, valine, isoleucine, leucine, methionine, and threonine. Non-limiting examples of enumerated amino acid type sets that are within the scope of such an embodiment include the set (alanine, valine), (alanine, valine, isoleucine), (methionine, threonine), and (valine, isoleucine, leucine).

Referring to block 206 of FIG. 2A, in some embodiments, the enumerated amino acid set consists of three or more of the group consisting of alanine, valine, isoleucine, leucine, methionine, and threonine. Non-limiting examples of enumerated amino acid type sets that are within the scope of such an embodiment include the set (alanine, valine, isoleucine), (alanine, methionine, threonine), and (valine, isoleucine, leucine).

Referring to block 208 of FIG. 2A, in some embodiments, the enumerated amino acid type set consists of four or more of the group consisting of alanine, valine, isoleucine, leucine, methionine, and threonine. Non-limiting examples of enumerated amino acid type sets that are within the scope of such an embodiment include the set (alanine, valine, isoleucine, leucine), (alanine, methionine, threonine, and isoleucine), and (valine, isoleucine, leucine, and methionine).

The first plurality of residues of the target protein that is represented by the vertices 34 of the original graph G 20 is some subset of all the residues of the target protein. This is because, as discussed above, only a subset of the residues of the target protein have methyl groups in their side chains that could be isotopically $^{13}$C methyl labeled. As such, referring to block 218 of FIG. 2B, in some embodiments the target protein further comprises at least one, two, three, four, five, six, seven, eight, nine, ten, eleven, twelve, thirteen, fourteen, fifteen, sixteen or seventeen different amino acid types that are not in the enumerated amino acid type set in addition to amino acid types that are in the enumerated amino acid type set.

Because each respective vertex 34 in G represents a different residue 38 in the first plurality of residues, it can therefore be assigned the amino acid type 40 of this different residue 38. Thus, consider the case in which the target protein has an alanine residue at position 138 in the primary sequence representation of the target protein, that this alanine is isotopically $^{13}$C methyl labeled, and that it is uniquely represented by a particular vertex 34 in the original graph 20. In this instance the residue assignment 38 of this particular vertex 34 is the alanine residue at position 138 in the primary sequence whereas the amino acid type assignment 40 of this particular vertex is "alanine." That is, while the amino acid type assignment 40 for a given vertex 34 is unambiguously derived from the corresponding residue assignment 38, the amino acid type assignment 40 does not identify which residue (which alanine in this example) in the target protein the given vertex 34 represents. Because the amino acid type assignment 40 of a given vertex 34 can be unambiguously derived from the residue assignment 38, in some instances the first data construct 20 does not explicitly store or retain amino acid type assignments 40, but rather calculates them from the residue assignments 38.

Turning to the edges 42 of original graph G, as discussed above, each respective edge 42 in G uniquely represents a pair of vertices in G that are within a threshold distance of each other in the atomic model 12. As discussed above, and referring to block 203 of FIG. 2A, in some embodiments each respective edge G is assigned a first edge type when the pair of vertices represented by the respective edge are for a geminal pair of methyls in the atomic model and is assigned a second edge type otherwise.

Referring to block 212 of FIG. 2A, in some embodiments the atomic model of the target protein that is used as the basis for constructing original graph G includes spectroscopically determined coordinates for each atom of all or a portion of the target protein. For instance, in some embodiments, the coordinates for each atom of the target protein or the portion of the target protein are determined by nuclear magnetic resonance, x-ray crystallography, or electron microscopy (block 214). In some embodiments, the atomic coordinates for the target protein are a set of three-dimensional coordinates $\{x_1, \ldots, x_N\}$ for a crystal structure of the target protein resolved (e.g., by X-ray crystallographic techniques) at a resolution of 3.3 Å or better, 3.2 Å or better, 3.1 Å or better, 3.0 Å or better, 2.5 Å or better, 2.2 Å or better, 2.0 Å or better, 1.9 Å or better, 1.85 Å or better, 1.80 Å or better, 1.75 Å or better, or 1.70 Å or better. In some embodiments, the atomic model of the target protein is the spatial coordinates of an ensemble of ten or more, twenty or more or thirty or more three-dimensional coordinates for the target protein determined by nuclear magnetic resonance where the ensemble has a backbone RMSD of 1.0 Å or better, 0.9 Å or better, 0.8 Å or better, 0.7 Å or better, 0.6 Å or better, 0.5 Å or better, 0.4 Å or better, 0.3 Å or better, or 0.2 Å or better. In some embodiments the atomic coordinates of the target protein are determined by neutron diffraction or cryo-electron microscopy.

In some embodiments, the target protein comprises two different types of polymers, such as a nucleic acid bound to a protein. In some embodiments, the target protein includes two polypeptides bound to each other. In some embodiments, the target protein under study includes one or more metal ions (e.g. a metalloproteinase with one or more zinc atoms).

Figure 2B:
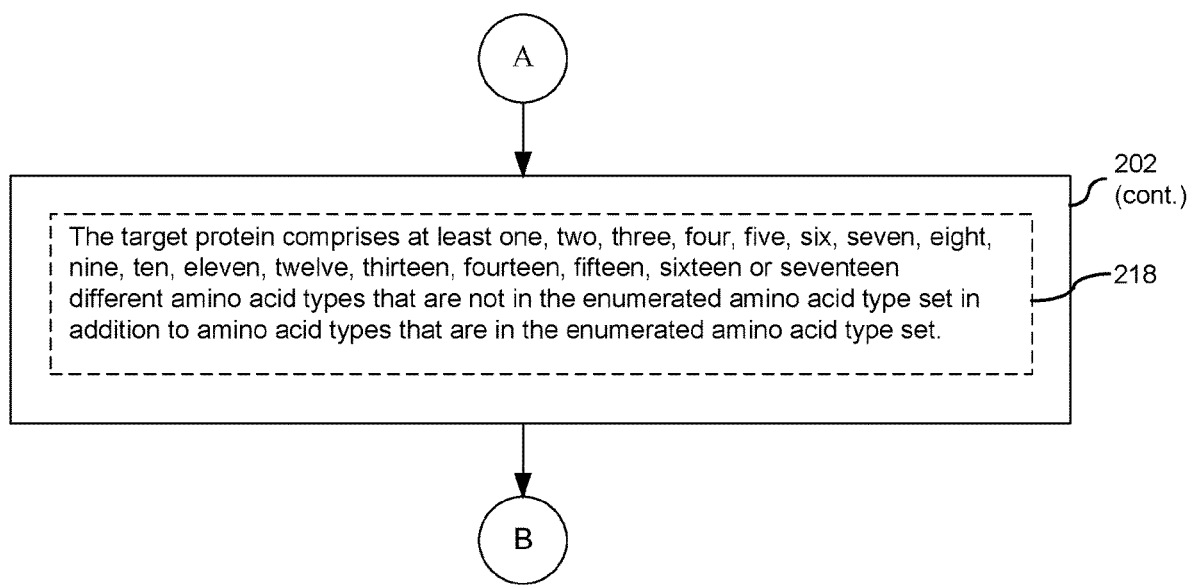

Referring to block 216 of FIG. 2B, in some embodiments, the atomic model of all or a portion of the target protein is determined from homology modeling of spectroscopically determined atomic coordinates of all or a portion of one or more second proteins other than the target protein.

In some such embodiments, the atomic coordinates of the target protein are determined using modeling methods such as ab initio methods, de novo methods (e.g., Jones, 1994, "De novo protein design using pairwise potentials and a genetic algorithm," 3: 567-574), density functional methods, semi-empirical and empirical methods, molecular mechanics, chemical dynamics, or molecular dynamics. See, for example, Ponders and Case, 2003, "Force Fields for Protein Simulations," Advances in Protein Chemistry 66, 27-78, which is hereby incorporated by reference.

In some embodiments, the atomic model of the target protein is represented by the Cartesian coordinates of the centers of the atoms comprising the target protein. In some alternative embodiments, the spatial coordinates for the target protein are represented in the atomic model of the target protein by the electron density of the target object as measured, for example, by X-ray crystallography. For example, in some embodiments, the atomic model of the target protein is represented by a $2F_{observed}-F_{calculated}$ electron density map computed using the estimated atomic coordinates of the target protein, where $F_{observed}$ is the observed structure factor amplitudes of the target object obtained by X-ray crystallographic measurement of one or more crystals comprising the target protein and Fe is the structure factor amplitudes calculated from the calculated atomic coordinates of the target protein.

Thus, the atomic model 12 for the target protein may be received as input data from a variety of sources, including, but not limited to, structure ensembles generated by solution NMR, co-complexes as interpreted from X-ray crystallography, neutron diffraction, cryo-electron microscopy, sampling from computational simulations, homology modeling or rotamer library sampling (e.g., Lovell, 2000, "The Penultimate Rotamer Library," Proteins: Structure Function and Genetics 40, 389-408), or any combination of these non-limiting techniques.

Figure 2C:
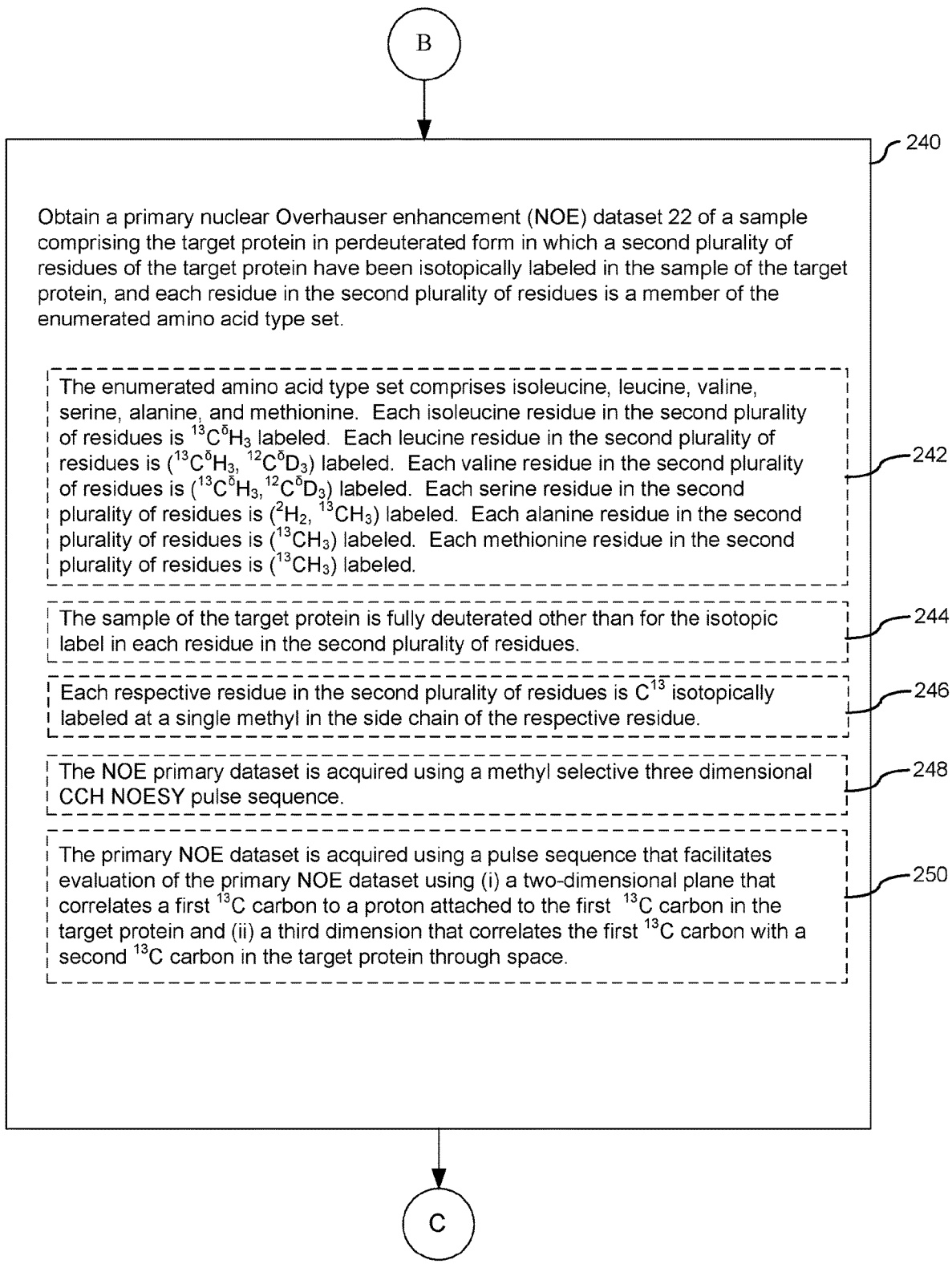

Referring to block 240 of FIG. 2C, a primary nuclear Overhauser enhancement (NOE) dataset 22 of a sample comprising the target protein is obtained. This data set may be preexisting or actively measured. In typical embodiments, the NOE dataset is acquired using a perdeuterated form of the target protein in which a second plurality of residues of the target protein have been isotopically labeled in the sample of the target protein. As in the case of the first plurality of residues that form the vertices of the original graph G, each residue in this second plurality of residues is a member of the enumerated amino acid type set.

For example, if the enumerated amino acid type set is (ILE, LEU, VAL) each residue in the second plurality of residues is a different ILE, LEU, or VAL in the primary sequence of the target protein. Referring to block 242, in a specific example the enumerated amino acid type set comprises isoleucine, leucine, valine, serine, alanine, and methionine. Each isoleucine residue in the second plurality of residues is $^{13}C\delta H_3$ labeled. Each leucine residue in the second plurality of residues is ($^{13}C\delta H_3$, $^{12}C\delta D_3$) labeled. Each valine residue in the second plurality of residues is ($^{13}C\delta H_3$, $^{12}C\delta D_3$) labeled. Each serine residue in the second plurality of residues is ($^2H_2$, $^{13}CH_3$) labeled. Each alanine residue in the second plurality of residues is ($^{13}CH_3$) labeled. Each methionine residue in the second plurality of residues is ($^{13}CH_3$) labeled.

Referring to block 244 of FIG. 2C, in some embodiments, the sample of the target protein is fully deuterated other than for the isotopic label in each residue in the second plurality of residues. Referring to block 246, in some embodiments, each respective residue in the second plurality of residues is $C^{13}$ isotopically labeled at a single methyl in the side chain of the respective residue.

Referring to block 248 of FIG. 2C, in some embodiments the NOE primary dataset 22 is acquired using a methyl selective three dimensional CCH NOESY pulse sequence. See, for example, Zwahlen et al., 1998, "An NMR Experiment for Measuring Methyl-Methyl NOEs in $^{13}C$-Labeled Proteins with High Resolution," J. Am. Chem. Soc. 120 (30), pp. 7617-7625, which is hereby incorporated by reference. In some embodiments, the primary NOE dataset 22 is acquired using a 3D SOFAST HMQC-NOESY-HMQC or 3D SOFAST NOESY-HMQC protocol. See, for example, Xia et al., 2016, "$^{15}N$ and $^{13}C$-SOFAST-HMQC editing enhances 3D-NOESY sensitivity in highly deuterated, selectively [$^1H,^{13}C$]-labeled proteins," Journal of Biomolecular NMR, 1-13, which is hereby incorporated by reference.

Referring to block 250, in some embodiments, the primary NOE dataset 22 is acquired using a pulse sequence that facilitates evaluation of the primary NOE dataset using (i) a two-dimensional plane that correlates a first $^{13}C$ carbon to a proton attached to the first $^{13}C$ carbon in the target protein and (ii) a third dimension that correlates the first $^{13}C$ carbon with a second $^{13}C$ carbon in the target protein through space.

Referring to block 270 of FIG. 2D, in the systems and methods of the present disclosure, a plurality of cross peaks in the primary NOE dataset 22 are identified. Each respective cross peak 62 in the primary NOE dataset 22 is generated by a NOE interaction between an isotopic label in a different first residue and an isotopic label in a different second residue in the second plurality of residues. As an example, consider the case in which a target protein has been $^{13}C$ isotopically labeled on a methyl in each leucine side chain and each isoleucine in its primary sequence. Further still, consider the case where this target protein has a leucine at position 100 (Leu 100) and an isoleucine at position 150 (Ile 150) in its primary sequence and further still that the $^{13}C$ labeled methyl of Leu 100 is within 10 Angstroms of the $^{13}C$ labeled methyl of Ile 150 in the target protein. This should give rise to a NOE interaction between that two methyl groups in the form of a cross peak 62 in the primary NOE dataset 22. As such, there can be as many cross peaks as there are NOE interactions between labeled $^{13}C$ methyl groups in the target protein, where each such interaction is manifested as a cross peak 62 in a particular region of the primary NOE dataset 22 that is characteristic of such methyl-methyl NOE interactions. In practice, in many instances not all the theoretically possible methyl-methyl NOE interactions give rise to a discernable cross peak 62 in the primary NOE dataset 22. Nevertheless, for some target proteins that can be studied using the systems and methods of the present disclosure, and referring to block 272 of FIG. 2D, in some embodiments the plurality of cross peaks comprises 10, 20, 30, 40, 50, 60, 70, 80, 90, 100, 110, 120, 130, 140, 150 cross peaks 62, or more.

Referring to block 273 of FIG. 2D, in some specific embodiments, each residue in the second plurality of residues is $^{13}C$ isotopically labeled at a single methyl in the side chain of the residue. Further, the identification of cross peaks in the primary NOE dataset outline in block 270 comprises (i) identifying a plurality of C, C, H triplets in the primary NOE dataset. Each triplet is formed from (a) an interaction between a first $^{13}$C labeled carbon in a methyl in a side chain of a first residue and a proton covalently bound to the first $^{13}$C labeled carbon (e.g., a first $^{13}$C of a methyl and a hydrogen that is bonded to the first $^{13}$C methyl) and (b) an interaction between the first $^{13}$C labeled carbon and a second $^{13}$C labeled carbon in a methyl in a side chain of a second residue. In the specific embodiment, the triplets are symmetry filtered thereby identifying a reduced set of triplets. See, Withrich, 1986, NMR of Proteins and Nucleic Acids, John Wiley & Sons, Inc., which is hereby incorporated by reference. In the specific embodiment, the triplets in the reduced set are clustered using the second and third coordinates of each triplet in the reduced set thereby forming a plurality of clusters of triplets. Each respective cluster of triplets is then deemed to be a cross peak 62 in the plurality of cross peaks of the primary NOE dataset 22.

Referring to block 274 of FIG. 2D, once the primary NOE dataset 22 is acquired, another graph, termed the observed graph H 24, is formed. As in the case of the original graph G 20, the observed graph H has one vertex per $^{13}$C isotopically labeled methyl. However, rather than using the atomic model, cross peaks 62 in the NOE NMR are used to form the vertices in the manner disclosed below. As such, a second data construct comprising an observed graph H is formed from the plurality of cross peaks 62. The observed graph H comprises a second plurality of vertices and a second plurality of edges. While each respective vertex 30 in the second plurality of vertices represents a different residue in the second plurality of residues, it is not initially known which residue (e.g., which $^{13}$C labeled methyl) the vertex 30 represents. In other words, it is not known which methyl in H corresponds to which methyl in G. This is precisely the problem that needs to be addressed.

Continuing with the block type analogy, graph H is formed by associating a unique color with each amino acid (block type) that has been selectively $^{13}$C methyl isotopically labeled. Each vertex 30 of graph H 24 is then colored with one or more colors (amino acid type assignment 102), corresponding to the amino acid types of the candidate originating amino acids for the methyl (vertex). For $^{13}$C isotopically labeled methyls originating in isoleucine or alanine amino acids the originating amino acid type 102 can be identified with significantly high confidence and thus the label 102 of the associated vertex 98 of graph H 24 can be labeled with the color (amino acid type) of the originating amino acid. For some of the selectively labeled methyls originating from leucine and valine amino acid residues, though, when it is not possible to determine with confidence the originating amino acid type using data from the primary NOE dataset experiment alone, the vertex is labeled with two colors. In other words, the vertex will have more than one assignment 100, with each such assignment representing a different amino acid type assignment 102 (e.g., LEU and VAL, etc.). In some embodiments, one or more secondary, separate conventional NMR experiments can disambiguate the possible amino acid assignments for a given vertex 98, in which case all the vertices 30 of the observed graph H end up with a unique color (amino acid assignment). In other words, in such situations, all the vertices 30 of the observed graph H end up with a single unique amino acid type 102.

Regarding the edges 30 of the observed graph H, as discussed above in the block type analogy, for each heard harmonic one can associate a small number of candidate-pairs of methyls (primary tones) (pair of vertices 30 of graph H), such that the pair of methyls whose interaction is actually generating the harmonic is one of the candidate-pairs of methyls. In practice, for roughly half of these harmonics (for roughly half of the cross peaks 62 in the primary NOE data set) the set of candidate-pairs has only one element, e.g., there is only one candidate. As an example, in one instance it is determined that a given cross peak 62 for the pair of vertices 30 graph H must be between the $^{13}$C labeled methyl of an isoleucine and the $^{13}$C labeled methyl of a valine. In this instance, the pair of vertices that are associated with this cross peak are respectively and singularly typed as isoleucine and valine. It is still know known which isoleucine and valine in the primary sequence of the target protein these pair of vertices represent, but at least each vertex in the pair of vertices has been assigned to a single amino acid type.

In addressing the construction of the edges of the observed graph H, to simplify exposition, the unrealistic assumption is first made that, for all heard harmonics (for each cross peak 62), there is only one candidate-pair of amino acid types that can be assigned to the pair of vertices 30 that correspond to each heard harmonic. Under such an assumption, for each heard harmonic (cross peak 62) a line can be drawn connecting its two methyls, e.g., the two methyls in the unique candidate-pair. In such an instance, turning to FIG. 1D, where each edge is associated with a cross peak represented by the edge 62, if a line is drawn connecting two methyls, then this cross peak is associated with the two respective vertices 98 of graph H as a possible assignment for the vertex 30.

In some embodiments, if the harmonic's intensity is above a certain threshold, this is interpreted as an indication that the harmonic originated from a geminal pair of methyls and is thus assigned a first edge type (e.g., red ink), otherwise the edge 106 is assigned a second edge type (e.g., blue ink). As discussed above, there are secondary NMR experiments that can be used in some embodiments to determine which interactions come from geminal pairs of methyls. If this secondary NMR data is available, then the red edges (the first edge type) of H can be assigned using this secondary NMR data, and all non-geminal heard harmonics in the NOE data are painted blue (assigned the second edge type).

As such, in other words, each respective edge 106 in the second plurality of edges of the observed graph H 24 represents a corresponding cross peak 62 in the plurality of cross peaks. Each respective vertex 30 is assigned one or more amino types in the enumerated amino acid type set using amino acid type assignments made by the primary NOE dataset or one or more secondary NMR datasets taken of the target protein.

Figure 4:
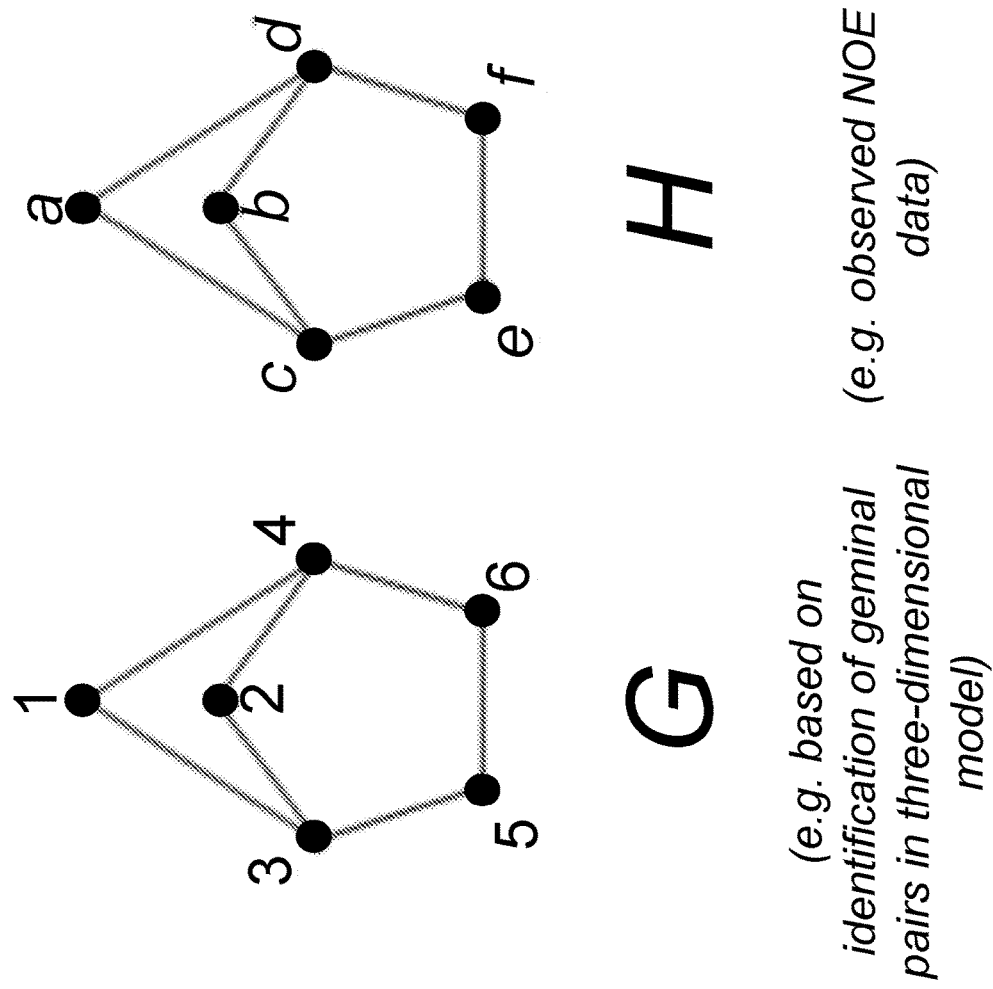
FIG. 4 depicts an original graph G and an observed graph H in accordance with some embodiments.

Ideally, the graph H is identical to the graph G. Even in that case, mapping H to G correctly is computationally non-trivial. In fact, the simplified version of the problem in which there are no colors, e.g., all dots and lines are simply black, is an instance of the famous graph isomorphism problem. In the graph isomorphism problem, the challenge is to determine whether two apparently different graphs can be rearranged to be identical. Even if G is identical to H there may be multiple valid mappings between the two. For example, if the graph on the left in FIG. 4 is considered graph G and the graph on the right is considered graph H, one valid mapping of H onto G can made by taking the image on the right and setting it on top of the image on the left, i.e., a→1, b→2, c→3, d→4, e→5, and f→6. But another valid mapping can be had if, prior to setting the image on the right on top of the image on the left, one first rotates the right image along the vertical axis, e.g., a→1, b→2, c→4, d→3, e→6, and f→5.

For graphs corresponding to original graphs of target proteins, for virtually every target protein, if one were lucky enough to measure all the possible harmonics (to detect all the NOE interactions between proximate isotopically $^{13}C$ labeled methyl groups in the target protein as cross peaks 62), e.g., G=H, then even without any color information for H (without any edge type identification 112), there would be a unique mapping of H into G. In such situations one may presume that this mapping could be readily identified. In reality, though, this is typically not the case. The graph H 24 formed from the primary NOE data set 22 is a faded copy of graph G 20.

The operations by which graph G 20 is faded to become graph H 24 arise from amino acid uncertainly, non-observation of NOE data, and geminal pair attenuation. The specific effects of these factors have on graph H are set forth below in Table 1.

TABLE 1

Effect on Graph H

| Effect | Cause of the Effect |
|---|---|
| 1. Assign multiple amino acid type assignments 102 to a given vertex 30, besides its true amino acid type assignments | Amino acid type uncertainty |
| 2. Delete edges 106 | Non-observation of cross-peaks 62 in the primary NOE dataset 22 |
| 3. Turn edges from the first edge type (red edges) to the second edge type (blue edges) | Geminal Pair Attenuation |

The rationale for each transformation is as follows. For amino acid uncertainty, as mentioned, sometimes the type of amino acid that contains a $^{13}C$ labeled methyl cannot be definitively determined for a given amino acid in the target protein from the primary NOE dataset 22. Nevertheless, one can always be sufficiently conservative to make sure that the correct amino acid type assignment is one of the amino acid type assignments assigned to the vertex 30. Non-observation arises because, as mentioned, in typical NOE experiments, 60-70% of all potential harmonics are not observed and it is typically not possible to predict which ones will be observed and which not. Geminal pair attenuation arises rarely, and typically due to human error, causing a geminal-pair harmonic to not be as strong as typical, and thus causing it to be mistaken for an ordinary harmonic.

Notably the following two operations listed in Table 2 below are not performed in the systems and methods of the present disclosure

TABLE 2

Operations that are not performed.

| Introduce edges into graph H that have no corresponding edge in graph G | Spurious Observation |
|---|---|
| Turn blue edges into a red edge (misidentify the edge type 112 of any edge 106 in graph H) | Non-Geminal Pair Amplification |

Even though the operations in Table 2 can, in principle, happen, their probability is very small. At the same time, allowing these possibilities makes the computational problem significantly more difficult. Realizing that there is a significant computational complexity asymmetry between allowing edges to be deleted (false negatives) versus allowing edges to be introduced (false positives) and ignoring the possibility of the latter is an important element of the disclosed systems and methods.

Referring to block 276 of FIG. 2D, in some embodiments, a respective edge 106 in the second plurality of edges of the observed graph H 24 is assigned a first edge type when the respective cross peak 62 in the plurality of cross peaks of the primary NOE dataset 22 corresponding to the respective edge 106 satisfies an intensity threshold and is otherwise assigned the second edge type. The first edge type signifies that the cross peak 62 corresponding to the edge 106 is generated in the primary NOE dataset 22 by a NOE interaction between a first $^{13}C$ labeled methyl group and another methyl group that is in the same residue (geminal methyl pair) as the first $^{13}C$ labeled methyl group (e.g., $^{13}C$ methyl labeled interacting with another methyl in the same valine, leucine, or isoleucine residue) in the target protein. The second edge type signifies that the cross peak 62 corresponding to the edge 106 is not generated in the primary NOE dataset 22 by a NOE interaction between a first $^{13}C$ labeled methyl group and another methyl group that is in the same residue (geminal methyl pair) as the first $^{13}C$ labeled methyl group.

Referring to block 277 of FIG. 2D, in some embodiments, the second plurality of vertices of the observed graph H 24 is less than the first plurality of vertices of the original graph G 20. In other words, graph H is a faded form of original graph G in which some of the vertices in graph H are missing, relative to graph G, due to failure to confidently identify $^{13}C$ methyl groups in the primary NOE dataset 22 that correspond to the missing vertices. As such, in these embodiments, while graph H has fewer vertices than graph G, each vertex in graph H represents a corresponding vertex in graph G (with the problem remaining of determining which vertex in graph G corresponds to any given vertex in graph H, e.g., the methyl assignment problem).

Referring to block 278 of FIG. 2D, in some embodiments, at least one vertex 30 in the second plurality of vertices of the observed graph H 24 is assigned two or more amino types in the enumerated amino acid type set through amino acid type assignments made by the primary NOE dataset 22 or one or more secondary NMR datasets taken of the target protein. In some embodiments, at least five percent of the vertices 30 in the second plurality of vertices of the observed graph H 24 are assigned two or more amino types in the enumerated amino acid type set through amino acid type assignments made by the primary NOE dataset 22 or one or more secondary NMR datasets taken of the target protein. In some embodiments, at least ten percent, at least twenty percent, or at least thirty percent of the vertices 30 in the second plurality of vertices of the observed graph H 24 are assigned two or more amino types in the enumerated amino acid type set through amino acid type assignments made by the primary NOE dataset 22 or one or more secondary NMR datasets taken of the target protein.

In some embodiments, at least one vertex 30 in the second plurality of vertices of the observed graph H 24 is assigned a single amino type in the enumerated amino acid type set while the remainder of the vertices are assigned two or more amino acid type assignments through amino acid type assignments made by the primary NOE dataset 22 or one or more secondary NMR datasets taken of the target protein. In some embodiments, at least five percent of the vertices 30 in the second plurality of vertices of the observed graph H 24 are assigned a single amino type in the enumerated amino acid type set while the remainder of the vertices are assigned two or more amino acid type assignments through amino acid type assignments made by the primary NOE dataset 22 or one or more secondary NMR datasets taken of the target protein. In some embodiments, at least ten percent, at least twenty percent, or at least thirty percent of the vertices 30 in the second plurality of vertices of the observed graph H 24 are assigned a single amino type in the enumerated amino acid type set while the remainder of the vertices are assigned two or more amino acid types in the enumerated amino acid type set using amino acid type assignments made by the primary NOE dataset 22 or one or more secondary NMR datasets taken of the target protein.

Referring to block 279 of FIG. 2E, a plurality of placements of the observed graph H onto the original graph G is made. If reality has conformed to the model, e.g., if indeed H was generated by G by applying (any) set of permissible transformations that systems and methods of the present disclosure allow (set forth in Table 1), then the task is to find a mapping of each vertex of H to a different vertex of G such that the following holds:

1. If vertex v 30 of graph H 24 is mapped to a vertex w 34 of graph G 20, then the amino acid type assignment 40 of vertex w must be one of the amino acid assignments 102 predicted for vertex v 30 in graph H.

2. If {a, b} is an edge 106 between vertices a and b of graph H and the mapping a→v and b→w is made (as part of a placement of graph H onto graph G), where v and w are vertices of graph G, then {v, w} must be an edge of G (between vertices v and w).

If reality has conformed to the disclosed model, there is always at least one mapping that satisfies all both of these constraints, namely the true mapping that corresponds to reality. On the other hand, there may well be multiple mappings that satisfy all the constraints (valid). As an extreme case, if all edges of G are deleted and all vertex-color sets in graph H include all four colors (e.g., there are four differ amino acid assignments 102 for each vertex 30), then all n!=n(n−1) . . . 2·1 possible mappings are valid.

As such, each respective placement 114 in the plurality of placements (i) includes a plurality of mappings and (ii) maps all the vertices of the observed graph H onto different vertices in the original graph G. Each mapping 97 in the plurality of mappings assigns a vertex 30 in the observed graph H to a vertex 34 in the original graph G. Each respective placement in the plurality of placements is subject to the set of constraints described above and rearticulated here. This set of constraints includes the constraint that, when a vertex v 30 in the observed graph H 24 is mapped to a vertex w 34 in the original graph G 20, the amino acid type assigned vertex w 40 in the original graph G is in the one or more amino acid types 102 assigned vertex v. The set of constraints further requires that, for an observed edge {a, b} between a vertex a and a vertex b in the observed graph H, when vertex a is mapped to a vertex v and vertex b is mapped to a vertex w in the original graph G, there exists an edge {v, w} between the vertex v and the vertex w in the original graph G.

Figure 5:
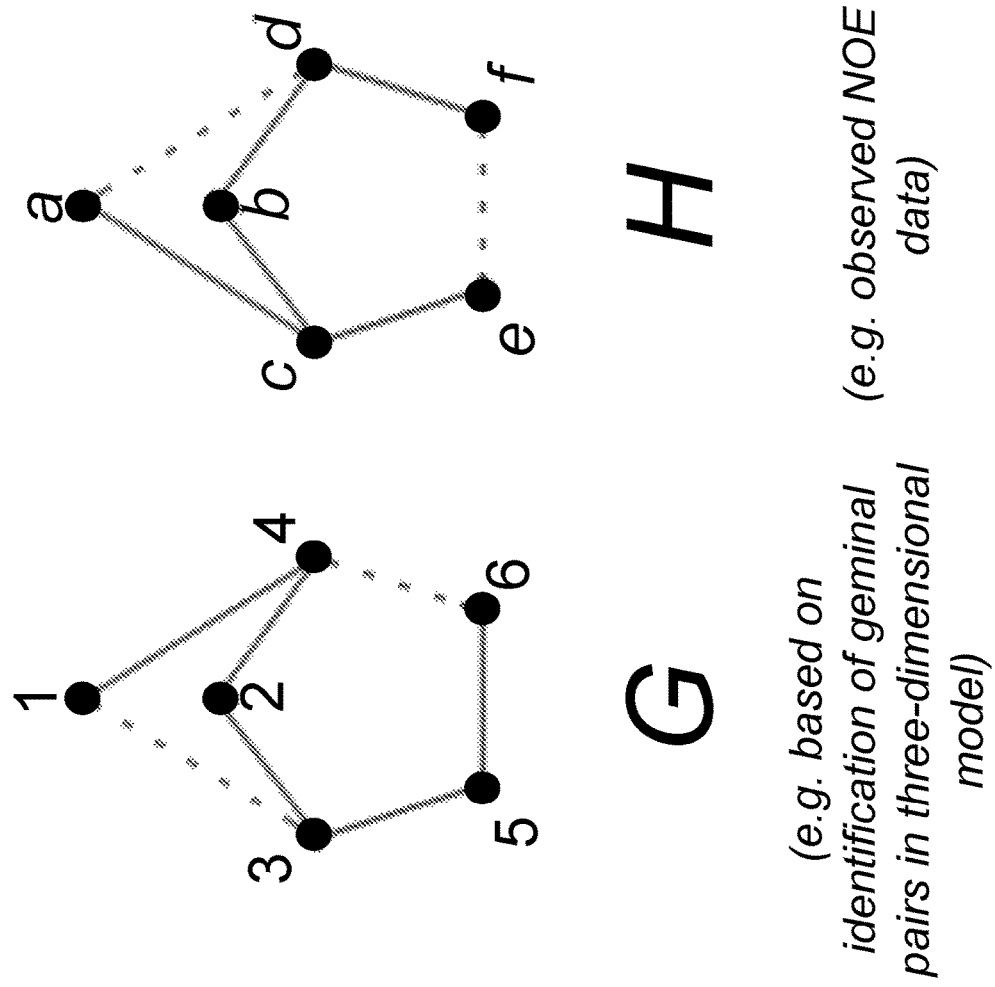
FIG. 5 illustrates the assignment of edge types in an original graph G and an observed graph H in accordance with some embodiments.

Referring to block 280 of FIG. 2E, in those embodiments, using the block type analogy, where edges in graph G and graph H were each assigned the color red or blue, in some embodiments, the set of constraints imposed on each respective placement 111 further includes the constraint that, if {a, b} is a red edge of graph H (meaning that it joins a geminal pair of methyls), then {v, w} must be a red edge of G. In other words, in such embodiments, the set of constraints further requires that when the edge {a, b} in the observed graph H is assigned a first edge type (red, indicating a geminal methyl pair) it must map to an edge {v, w} in the original graph G that is the first edge type. Because the observed graph H can be considered a faded copy of the original graph G, it is not the case that when the edge {a, b} in the observed graph H is assigned a second edge type (blue, indicating that it is representing a non-geminal pair of methyls) it must map to an edge {v, w} in the original graph G that is the first edge type. That is to say, if an edge 42 in the observed graph H connects a pair of geminal methyls, the set of constraints requires that the corresponding edge in graph G according to the placement must also be one that has been identified as between geminal methyls. However, conversely, if an edge in the observed graph H does not connect a pair of geminal methyls, the set of constraints does not require that the corresponding edge in the original graph G in accordance with the placement also be one that has been identified as not being between geminal methyls. It could for instance be the case that the data used to form the observed graph H (the NMR data) simply did not detect that the pair of methyls were a geminal pair. The situation is illustrated in FIG. 5, where the set of constraints imposes that requirement that dashed edges in H (representing geminal methyl pairs) can only map to dashed edges in G (representing edges between vertices that are within a first threshold distance of each other) and non-dashed edges in H (representing non-geminal methyl pairs) can map to either dashed or non-dashed edges in G.

Referring to block 281 of FIG. 2E, in some embodiments, the threshold distance used for identifying edges between vertices 34 in the original graph G is initially 10 Å. In other embodiments, the threshold distance used for identifying edges between vertices 34 in the original graph G is initially a value selected between 5 Å and 12 Å. In still other embodiments, the threshold distance used for identifying edges between vertices 34 in the original graph G is initially a value selected between 6 Å and 11 Å. Referring to block 282, of FIG. 2E, in some embodiments, this threshold distance is increased from the initial distance to a larger distance when the creating of block 279 fails to create a first threshold number placements for the plurality of placements. The threshold distance is decreased from the initial distance to a smaller distance when the creating of block 279 creates more than a second threshold number placements for the plurality of placements. The values for the first threshold number of placements and the second threshold number of placements is application dependent.

Bundles, Balls in Boxes, and Strings.

As mentioned above, in general, a unique methyl-pair candidate cannot be identified for each NOE measurement (harmonic, cross peak 62). So, in general, if there are k candidates, these correspond to k edges in H and this collection of k edges is referred to herein as a "bundle." Assuming, that the methyl-pair actually giving rise to each harmonic is present in the harmonic's bundle, the task becomes to map the vertices of H to the vertices of G so that at least one edge from each bundle is mapped to an edge of G.

Alternatively, the entire setting can be represented as follows. Imagine each methyl (sensor) in the original target protein as a box in three-dimensional space, having the color of its originating amino acid. Imagine each heard tone as a simple ball, colored with one or more color(s), corresponding to its potential originating amino acid. We need to place the balls in the boxes so that each ball is placed in a box whose color is one of the ball's colors. Each heard harmonic selects one or more pairs of balls (a bundle of pairs) and ties the two balls in each pair with a string of the predetermined threshold d (e.g. 10 Å). The task at hand is to find a placement of the balls into the boxes such that from each bundle, at least one of the strings is not broken.

To address this task, referring to block 283 of FIG. 2E, each set in a plurality of sets 32 is initialized (e.g., to zero). Each set 32 in the plurality of sets represents a different vertex 30 in the observed graph H. Then, referring to block 284, a determination is made, for each respective set 32 in the plurality of sets, a number of different mappings for the vertex i 30 represented by the respective set in the observed graph H into the original graph G by polling the plurality of placements as a constraint satisfaction problem in which, for each respective possible assignment of the vertex i into the original graph G, when a determination is made that there exists a mapping 97 in the plurality of mappings that includes the respective assignment, the respective set 30 is advanced, and is not advanced otherwise.

The disclosed formulation is "conservative enough," e.g, the correct assignment (called the "ground truth") will nearly always respect the puzzle constraints and thus be deemed "valid." Equivalently, if a methyl assignment is not deemed valid in the disclosed systems and methods, then it is not the ground truth. On the other hand, the disclosed criterion shrinks the set of mappings. Specifically, even though the notion of validity, in general, does not uniquely determine the correct mapping, it unambiguously assigns 60-90% of all the methyls in a given target protein in some embodiments. In other words, even though there can be many valid mappings per the disclosed formulation, they all agree perfectly on 60-90% of all methyls. Therefore, as long as the ground truth is a valid mapping, something that is nearly always the case, the disclosed validity criterion alone determines with 100% accuracy and 100% certainty the correct assignment of 60-90% of all methyls in the polymer. For the remaining 10-40% of methyls, validity still dramatically reduces the set of possibilities: for a typical non-assigned methyl, the number of possibilities, on average, is between 2 and 3. In some embodiments, provides the correct assignment for at least 30 percent, at least 40 percent, at least fifty percent, at least sixty percent, at least seventy percent, at least eighty percent, or at least ninety percent of all the methyls. In fact, things are much better than that as discussed below.

FIGS. 1E and 6 illustrate. FIG. 6 illustrates a placement dataset comprising a plurality of placements each adhering to the set of constraints of the present disclosure. Each placement 114 includes a plurality of mappings that collectively map all the vertices of graph H onto vertices of graph G subject to the constraints of the present disclosure. Each mapping 97 in the plurality of mappings, therefore, assigns a vertex identifier 98 from the observed graph H to a corresponding vertex identifier 36 in the original graph G. In accordance with the constraints of the present disclosure, for each such mapping 97, it must be the case that the amino acid type 40 of the corresponding vertex 36 must be in the set of possible amino acid types 116 for the respective vertex in graph H. Upon completion of the evaluation of the constraint satisfaction problem, a determination is made for each respective vertex 34 in graph H across all the placements that were identified by the constraint satisfaction problem analysis, of how many different vertices 30 in graph H the respective vertex 34 was mapped to. For this analysis, there is no requirement that the constraint satisfaction problem examine all possible placements. Upon conclusion of the constraint satisfaction problem analysis, the array S for each respective vertex in the graph H, illustrated in FIG. 6, will have an integer value of zero, one, or greater than 1. If the integer value in S is zero for a given vertex in graph H, that means there is no possible solution for mapping that vertex onto graph H subject to the constraints of the present disclosure. If the integer value in S is one for a given vertex in graph H, that means the methyl corresponding to the vertex in graph H has been unambiguously assigned to a single vertex in graph G. If the integer value in S is two or greater for a given vertex in graph H, that means the methyl corresponding to the vertex in graph H has not been unambiguously assigned to a single vertex in graph G, but rather multiple solutions exists.

Advantageously, the disclosed systems and methods quickly determines the set of possibilities S) for every methyl. In other words, the disclosed systems and methods quickly determines the set of possibilities S) for every vertex in the graph H. To see why this is so, consider the case where the n vertices of graph G and the n vertices of graph H, arbitrarily, are labeled with the integers $[n]=\{1, 2, \ldots, n\}$. Then, one can think of a mapping as simply a placement $\pi$ of [n], where if, e.g., $\pi=22, 12, 1, \ldots, 32, 6$, this means that vertex 1 of H is mapped to vertex 22 of G, vertex 2 of H is mapped to vertex 12 of G, etc. Each valid placement 114 can be thought of as written as a row with n columns as illustrated, for example, in FIG. 7. For each $i \in [n]$, let S(i) be the set of distinct values written on column i. For example, saying that methyl i (vertex 30 of graph H) is assigned means that $|S(i)|=1$.

In some embodiments, to determine the sets S(i) quickly the problem "Find a valid mapping of H into G" is expressed as a constraint satisfaction problem (CSP) as discussed in relation to block 279 of FIG. 2E. Methods for solving such problems are known as CSP-solvers. The development of efficient CSP-solvers is an active area of computer science, where resources and thinking have been invested in order to solve problems unrelated to chemistry. By formulating the methyl assignment problem in this manner all that effort is leveraged, as several excellent CSP-solvers exist in the public domain. So, in some embodiments of the systems and methods of the present disclosure, block 279 of FIG. 2E is executed in the following manner:

For every $i \in [n]$, let $P(i)=[n]$ and let $S(i)=\emptyset$.
For every $i \in [n]$ do
  Set complete to False
  While not complete do
    Ask the CSP-solver for a valid mapping $\pi$ such that $\pi(j) \in P(j)$ for every $j \in [n]$
    If the CSP-solver says that none exist set complete to True
    Otherwise, remove $\pi(i)$ from $P(i)$ and add it to $S(i)$ Such an approach runs contrary to the conventional approaches of solving the methyl assignment problem. Such conventional approaches can be analogized to the conventional ways in which Sudoku puzzles are solved. Conventionally, Sudoku puzzles (and by analogy the methyl assignment problem) is addressed in the following manner. By considering the constraints directly relevant to each empty square, what is sought is the identity of an empty square for which the set of possible numbers can be whittled down to 1. This square is filled out in the hopes that doing so will help to whittle down the possibilities for some other empty square to 1. Truly difficult Sudoku puzzles (akin to the disclosed methyl assignment problem) do not yield to this approach. Even though there is a unique solution to the entire problem, and even though one can whittle down the number of possible numbers for each square down to perhaps two or three, there is no square that can be reduced to 1 possibility by considering only the directly relevant constraints. Determining any particular square is actually assigned, e.g., that there really is only one possibility for it, involves making multi-step inferences across far away and seemingly not obviously relevant squares.

This is exactly the situation for the methyl assignment problem addressed by the systems and methods of the present disclosure. Namely, the systems and methods of the present disclosure provides a formulation of the methyl assignment problem as a puzzle that is solvable by computers. That is, one trained in solving the methyl assignment problem using conventional techniques looking at the disclosed definition of validity would agree that it does not exclude the ground truth, but would most likely find it very hard to believe that it assigns any methyl. The reason it takes a researcher several months to do the equivalent assignment of H onto G is precisely because the researcher has to repeatedly make a sequence of guesses, follow them to their logical conclusions and, if they reach a dead end (which happens most of the time), backtrack. Notably, to guide this blind search more efficiently, e.g., to restrict the guesses, they use physical chemistry knowledge that is very hard to teach to computers. If all that knowledge is stripped away, as is done in the definition of validity, their effort would become even more difficult.

Finally, besides dispensing with the need to understand (or teach a computer) physical chemistry, the disclosed systems and method work with NOE data that is much sparser than what is considered workable. This is a very serious advantage of the disclosed systems and methods, especially as larger and larger proteins are to be considered.

Referring to block 286 of FIG. 2F, a vertex 30 in the observed graph H is deemed to be uniquely assigned to a vertex 34 in the original graph G when the set 32 for the respective vertex 30 includes a single unique assignment upon completion of the determining 284. Referring to block 288 of FIG. 2F, in some embodiments, the disclosed systems and methods uniquely assigns at least forty, fifty, sixty, seventy, or eighty percent of the vertices 30 in the observed graph H to the original graph G.

Referring to block 290 of FIG. 2F, in some embodiments, the entity that interacts with the target protein is a second protein that binds with target protein and block 286 identifies a portion of a surface of the target protein that is bound by the second protein. This is possible once the vertices (methyls) in graph H have been assigned, because it allows for pairs of NMR experiments to be performed in which one NMR experiment is of the target protein and the other NMR experiment is of the target protein in the presence of the entity. The entity will bind a portion of the surface of the target protein, and the peaks corresponding to the methyls in the immediate presence of this portion of the surface will shift in the target protein plus entity NMR experiment with respect to their corresponding peaks in the target protein only NMR experiment. Conversely, the peaks corresponding to the methyls not in the immediate presence of this portion of the surface of the target protein will not shift in the target protein plus entity NMR experiment with respect to their corresponding peaks in the target protein only NMR experiment. In this way, the region of the surface of the target protein that binds the entity can be determined. Such an approach is one of many example ways to characterize a target protein or the interaction of a target protein with an entity once the methyl assignment problem has been addressed using the systems and methods of the present disclosure. Those of skill in the art will readily appreciate a number of other different ways of characterizing a target protein or the interaction of a target protein with an entity once the methyl assignment problem has been addressed using the systems and methods of the present disclosure and all such different ways are within the scope of the systems and methods of the present disclosure. See, for example Natarajan et al., 2017, "An allosteric site in the T-cell receptor Cβ domain plays a critical signaling role," Nature Communications, DOI: 10.1038/ncomms15260, which is hereby incorporated by reference.

Referring to block 292 of FIG. 2F, in some embodiments, the entity is an inhibitor that binds with target protein and block 286 identifies a portion of a surface of the target protein that is bound by the inhibitor. Referring to block 294 of FIG. 2F, in some such embodiments, the inhibitor has a molecular weight of less than 15000 Daltons, less than 10000 Daltons, of less than 5000 Daltons, less than 2500 Daltons, or less than 2000 Daltons.

Referring to block 296 of FIG. 2F, in some embodiments the entity is an inhibitor that binds with target protein and the inhibitor is a chemical compound that satisfies at least three, at least four, or all five of the Lipinski rule of five criterion: (i) not more than five hydrogen bond donors (e.g., OH and NH groups), (ii) not more than ten hydrogen bond acceptors (e.g. N and O), (iii) a molecular weight under 500 Daltons, and (iv) a Log P under 5. The "Rule of Five" is so called because three of the four criteria involve the number five. See, Lipinski, 1997, Adv. Drug Del. Rev. 23, 3, which is hereby incorporated herein by reference in its entirety. In some embodiments, the entity satisfies one or more criteria in addition to Lipinski's Rule of Five. For example, in some embodiments, the entity has five or fewer aromatic rings, four or fewer aromatic rings, three or fewer aromatic rings, or two or fewer aromatic rings.

Referring to block 298 of FIG. 2F, in some embodiments, the unique assignment of a first vertex 30 in the observed graph H to the original graph G is used to assign a first peak in the NOE dataset to a first residue in the atomic model and a second peak in the NOE dataset to a second residue in the atomic model. In such embodiments, the first peak and the second peak are not within the plurality of cross peaks and a $^{13}C$ labelled methyl of the first residue and a $^{13}C$ labelled methyl of the second residue are deemed to create the cross peak in the plurality of cross peaks represented by the first vertex.

Non-Assigned Methyls.

Observe that after determining the assigned vertices (both those in H and their corresponding vertices in G) they can be removed them from consideration. Assume now that there are t≤n non-assigned vertices and consider the following graph C on 2t vertices.

Draw t vertices (dots) on the left and t vertices on the right, retaining their original labels from [n].

From each vertex i on the left, draw a line to every vertex j∈S(i) on the right.

Clearly, C is a perfect representation of the sets S(i), e.g., it does not lose any information. Observe now that every valid mapping corresponds to a perfect matching of C, e.g., to a subset of exactly t edges of C such that every vertex is in exactly one edge. Therefore, the number of valid placements (mappings) equals the number of perfect matchings of C. As mentioned, this number can be very large, e.g., in the trillions. While, at first sight, this seems terrible, it is actually much better than it appears. The reason is as follows.

Pick any vertex of C on the left and, by following edges in C, try to travel to as many other vertices of C, in either side, as possible. If, in graph-theoretic lingo, C is connected, then you will be able to reach every vertex of C. If it is not, you will only be able to reach a subset of all vertices, called a connected component. Observe now the following: when it comes to forming perfect matchings, the different connected components do not interact. In other words, if C has k≥1 connected components, $C_1, C_2, \ldots, C_k$, then Perfect Matchings(C)=Perfect Matchings($C_1$)×Perfect Matchings($C_2$)× ... ×Perfect Matchings($C_k$) as illustrated in FIG. 7. In practice it is often the case that k≈4. So, even though perfect matchings (C) can be large, this number does not reflect the difficulty of choosing between the different options. For example, if there are four connected components and each one has ten perfect matchings, then the total number of valid solutions (complete mappings) is $10^4$ (a very discouraging number), but a human expert would only need to make four choices in order to find the best mapping, each choice requiring the selection of 1 matching from 10. Moreover, in typical cases where the number of valid solutions is astronomical, the reason is that there exist one or more connected components where nearly all connections between the two sides are present, e.g., regions of the protein with very poor coverage in terms of harmonics, causing the problem to be severely underdetermined. For example, if there are two such components of size 9 and 10, the number of valid solutions exceed a trillion. Modification of only the red parts is needed to achieve the stated goals of 1) describing the fixing of the vertex colors on H and 2) loosely defining the bundles concept.

Example

As a test case for the disclosed methods a recently acquired high-resolution NOE dataset for a 209-amino acid protein (Hsp90α), containing 18 leucines, 10 valines, 20 isoleucines in the primary sequence, for a total of 76 methyls, was used. The X-ray structure of the target protein was obtained from the Protein Data Bank ID: 1YER, Stebbins et al., 1997, Cell 89, 239-250, which is hereby incorporated by reference. The NOE dataset was collected on a sample of Hsp90α that had been selectively isotopically labelled on a single methyl group in the alanine, isoleucine, leucine, and valine (AILV) residues of the protein and thus 76 methyl peaks showed in a reference two-dimensional NMR spectrum of the protein sample, where each peak is defined by two coordinates ($^{13}$C, $^1$H).

The NOE data amounted to a methyl-selective three-dimensional CCH NOESY spectrum (Zwahlen et al., 1998, "An NMR Experiment for Measuring Methyl-Methyl NOEs in $^{13}$C-Labeled Proteins with High Resolution," J. Am. Chem. Soc. 120 (30), pp. 7617-7625) recorded on an 800 MHz NMR spectrometer, using a standard (incremental) sampling schedule with 32 milliseconds of total acquisition time in both indirect $^{13}$C dimensions for a resolution of 31.4 Hz.

Manual picking of the raw NOE data resulted in a set of 399 NOE C,C,H "triplets," each of which is referred to in this example as a datum. In order to derive a graph H of reliably observed NOE interactions the triplets were first filtered using the standard "symmetry check" process of NMR spectroscopy. See, Withrich, *NMR of Proteins and Nucleic Acids*, John Wiley & Sons, New York, 1986. Specifically, for each datum (triple) D the following was identified:

All methyl peaks within standard tolerances of the last two coordinates of the datum (0.1 ppm in $^{13}$C and 0.01 ppm in $_1$H) determines a set of candidate "receiver" methyl peaks for the datum. Let this set be denoted R(D).

All methyl peaks whose carbon coordinate is within standard tolerance (0.1 ppm) of the first coordinate of the datum determines a set of candidate "sender" methyl peaks for the datum. Let this set be denoted S(D).

Then for each possible candidate sender-receiver pair, e.g., each element (s, r) of S(D)×R(D), a complementary NOE datum is sought, e.g., one whose first coordinate is within standard tolerance of the carbon coordinate of r, and whose last two coordinates are within standard tolerances of the two coordinates of s. If the number of complementary pairs found in this manner was either 0 (no complementary datum) or greater than 1 (ambiguity in complementarity), the datum is discarded. As a result, the data (triplets) that remain after symmetry-filtering come in complementary pairs. One hundred eight such pairs remained.

For each complementary pair of triplets, the last two coordinates (C, H) of each triplet is referred to as a methyl signature. Thus, each complementary pair of NOE data represents an NOE interaction between two methyl signatures. If each methyl signature is considered as a point on the (C, H) plane, the signatures can be clustered, based on their distance, into (presumed) methyl peaks. This resulted in 70 clusters, giving rise to 70 vertices 30 for the observed graph H 24. That is, from the 76 methyls present in the primary sequence of the target protein, 70 participated in at least one unambiguous NOE connectivity so that the average degree of the resulting graph H was 3.08, having 70 vertices and 108 edges.

Note that, per the description above, the disclosed method in this example operates on the basis of the NOE data and the three-dimensional structure of the target protein without a requirement for a two-dimensional reference spectrum as input, in order to aggregate the methyl signatures into clusters corresponding to methyl peaks. In particular, it makes no assumptions regarding the number of possible peaks present in crowded regions of the spectrum.

Besides the NOE data (and input atomic structure), the only other information utilized is: (1) the residue type of each methyl peak, and (2) a specification of which NOEs arise from geminal connectivities (between the $\gamma_1/\gamma_2$ methyl peaks of Valines, and $\delta_1/\delta_2$ methyl peaks of Leucines).

Given all this information, the disclosed method returns a set of possible methyls for each vertex of the graph (cluster of methyl signatures/methyl peak). When the returned set has only one methyl, the vertex is considered to be unambiguously assigned. In all cases reported below, for every vertex (cluster of methyl signatures/methyl peak) the returned set of possible methyls contains the methyl assigned by the expert user (determined manually).

Specifically, given the information described above, the disclosed method unambiguously assigns 90% of the vertices (63 out of 70). If the residue type of each methyl peak is withheld, it unambiguously assigns 83% of the vertices. If the specification of which NOEs arise from geminal connectivities is withheld, it unambiguously assigns 80% of the vertices.

The ability to unambiguously assign 83% of the vertices without the residue type of each methyl identified is achieved by employing the disclosed method for predicting the residue type. The predictor may return more than one candidate residue types for a resonance and, even so, can make mistakes. In this data it did not make any mistakes, but predicted multiple types for several resonances.

Geminal connectivity information can be readily obtained via a complementary NOE experiment with a shorter mixing time.

CONCLUSION

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIGS. 1A, 1B, 1C, 1D, and/or 1E or described in FIG. 2. These program modules can be stored on a CD-ROM, DVD, magnetic disk storage product, USB key, or any other non-transitory computer readable data or program storage product.

The foregoing description, for purpose of explanation, has been described with reference to specific implementations. However, the illustrative discussions above are not intended to be exhaustive or to limit the invention to the precise forms disclosed. Many modifications and variations are possible in view of the above teachings. The implementations described herein were chosen and described in order to best explain the principles of the invention and its practical applications, to thereby enable others skilled in the art to best utilize the invention and various implementations with various modifications as are suited to the particular use contemplated.

What is claimed:

1. A computing system for characterizing a target protein or an interaction of the target protein with an entity, the computing system comprising one or more processors and memory storing one or more programs for execution by the one or more processors, the one or more programs singularly or collectively executing a method comprising:

(A) forming a first data construct comprising an original graph G from an atomic model of the target protein, the original graph G comprising a first plurality of vertices and a first plurality of edges, wherein
   each residue in a first plurality of residues of the target protein is a member of an enumerated amino acid type set,
   each respective vertex in the first plurality of vertices represents a different residue in the first plurality of residues and is further assigned the amino acid type, in the enumerated amino acid type set, of the different residue, and
   each respective edge in the first plurality of edges uniquely represents a pair of vertices in the first plurality of vertices that are within a threshold distance of each other in the atomic model, (B) obtaining a primary nuclear Overhauser enhancement (NOE) dataset of a sample comprising the target protein in perdeuterated form, wherein
   a second plurality of residues have been isotopically labeled in the sample of the target protein, and
   each residue in the second plurality of residues is a member of the enumerated amino acid type set;

(C) identifying a plurality of cross peaks in the primary NOE dataset, wherein each respective cross peak in the primary NOE dataset is generated by NOE interaction between an isotopic label in a different first residue and an isotopic label in a different second residue in the second plurality of residues;

(D) forming a second data construct comprising an observed graph H from the plurality of cross peaks, the observed graph H comprising a second plurality of vertices and a second plurality of edges, wherein
   each respective vertex in the second plurality of vertices represents a different residue in the second plurality of residues,
   each respective edge in the second plurality of edges represents a corresponding cross peak in the plurality of cross peaks, and
   each respective vertex in the second plurality of vertices is assigned one or more amino types in the enumerated amino acid type set using amino acid type assignments made by the primary NOE dataset or one or more secondary NOE NMR datasets taken of the target protein;

(E) creating a plurality of placements of the observed graph H onto the original graph G, wherein each respective placement in the plurality of placements (i) includes a plurality of mappings and (ii) maps all the vertices of the observed graph H onto different vertices in the original graph G, each mapping in the plurality of mappings assigning a vertex in the observed graph H to the original graph G, wherein each respective placement in the plurality of placements is subject to a set of constraints comprising:
   when a vertex v in the observed graph H is mapped to a vertex w in the original graph G, the amino acid type assigned vertex w in the original graph G is in the one or more amino acid types assigned vertex v, and
   for an observed edge {a, b} between a vertex a and a vertex b in the observed graph H, when vertex a is mapped to a vertex v and vertex b is mapped to a vertex w in the original graph G, there exists an edge {v, w} between the vertex v and the vertex w in the original graph G;

(F) initializing each set in a plurality of sets, each set in the plurality of sets representing a different vertex in the observed graph H;

(G) determining, for each respective set in the plurality of sets, a number of different mappings for the vertex i represented by the respective set in the observed graph H into the original graph G by polling the plurality of placements as a constraint satisfaction problem in which, for each respective possible assignment of the vertex i into the original graph G, when a determination is made that there exists a mapping in the plurality of mappings that includes the respective assignment, the respective set is advanced, and is not advanced otherwise; and (H) deeming a vertex in the observed graph H to be uniquely assigned to a vertex in the original graph G when the set for the respective vertex includes a single unique assignment upon completion of the determining (G).

2. The computing system of claim 1, wherein
each respective edge in the first plurality of edges is assigned a first edge type when the pair of vertices represented by the respective edge are for a geminal pair of methyls in the atomic model,
each respective edge in the first plurality of edges is assigned a second edge type when the pair of vertices represented by the respective edge are not for a geminal pair of methyls in the atomic model,
each respective edge in the second plurality of edges is assigned the first edge type or the second edge type, and
the set of constraints further comprises the constraint that, when the observed edge {a, b} in the observed graph H is assigned the first edge type, the edge {v, w} in the original graph G is also assigned the first edge type.

3. The computing system of claim 1, wherein the enumerated amino acid type set consists of two or more of the group consisting of alanine, valine, isoleucine, leucine, methionine, and threonine.

4. The computing system of claim 1, the method further comprising:
(I) using the unique assignment of a first vertex in the observed graph H to the original graph G to assign a first peak in the primary NOE dataset to a first residue in the atomic model and a second peak in the primary NOE dataset to a second residue in the atomic model, wherein
the first peak and the second peak are not within the plurality of cross peaks, and
a label of the first residue and a label of the second residue are deemed to create the cross peak in the plurality of cross peaks represented by the first vertex.

5. The computing system of claim 1, wherein the entity is a second protein that binds with target protein and the deeming (H) identifies a portion of a surface of the target protein that is bound by the second protein.

6. The computing system of claim 1, wherein the entity is an inhibitor that binds with target protein and the deeming (H) identifies a portion of a surface of the target protein that is bound by the inhibitor.

7. The computing system of claim 1, wherein the method uniquely assigns at least fifty percent of the vertices in the observed graph H to the original graph G.

8. The computing system of claim 1, wherein the plurality of cross peaks comprises twenty cross peaks.

9. The computing system of claim 1, wherein
the enumerated amino acid type set comprises isoleucine, leucine, valine, serine, alanine, and methionine,
each isoleucine residue in the second plurality of residues is $^{13}C^{\delta}H_3$ labeled,
each leucine residue in the second plurality of residues is ($^{13}C^{\delta}H^3$, $^{12}C^{\delta}D_3$) labeled,
each valine residue in the second plurality of residues is ($^{13}C^{\gamma}H_3$, $^{12}C^{\gamma}D_3$) labeled
each serine residue in the second plurality of residues is ($^{2}H_2$, $^{13}CH_3$) labeled,
each alanine residue in the second plurality of residues is ($^{13}CH_3$) labeled, and
each methionine residue in the second plurality of residues is ($^{13}CH_3$) labeled.

10. The computing system of claim 1, wherein the sample of the target protein is fully deuterated other than for the isotopic label in each residue in the second plurality of residues.

11. The computing system of claim 1, wherein each respective residue in the second plurality of residues is $^{13}C$ isotopically labeled at a single methyl in the side chain of the respective residue.

12. The computing system of claim 1, wherein the primary NOE dataset is acquired using a methyl selective three dimensional CCH NOESY pulse sequence.

13. The computing system of claim 1, wherein the primary NOE dataset is acquired using a pulse sequence that facilitates evaluation of the dataset using a (i) two-dimensional plane that correlates a first $^{13}C$ carbon to a proton attached to the first $^{13}C$ carbon in the target protein and (ii) a third dimension that correlates the first $^{13}C$ carbon with a second $^{13}C$ carbon in the target protein through space.

14. The computing system of claim 1, wherein each respective residue in the second plurality of residues is $^{13}C$ isotopically labeled at a single methyl in the side chain of the respective residue and the identifying the plurality of cross peaks in the primary NOE dataset comprises performing a procedure comprising:
(i) identifying a plurality of C, C, H triplets in the primary NOE dataset, wherein each C, C, H triplet is formed from (a) an interaction between a first $^{13}C$ labeled carbon in a methyl in a side chain of a first residue in the second plurality of residues and a proton covalently bound to the first $^{13}C$ labeled carbon and (b) an interaction between the first $^{13}C$ labeled carbon and a second $^{13}C$ labeled carbon in a methyl in a side chain of a second residue in the second plurality of residues,
(ii) symmetry filtering the plurality of C, C, H triplets thereby identifying a reduced set of C, C, H, triplets, and
(iii) clustering the C, C, H triplets in the reduced set of C, C, H triplets using the second and third coordinates of each respective C, C, H triplet in the reduced set of C, C, H triplets thereby forming a plurality of clusters of C, C, H triplets, wherein each respective cluster of C, C, H triplets is deemed to be a cross peak in the plurality of cross peaks in the primary NOE dataset.

15. A method for characterizing a target protein or an interaction of the target protein with an entity, the method comprising:
(A) forming a first data construct comprising an original graph G from an atomic model of the target protein, the original graph G comprising a first plurality of vertices and a first plurality of edges, wherein
each residue in a first plurality of residues of the target protein is a member of an enumerated amino acid type set,
each respective vertex in the first plurality of vertices represents a different residue in the first plurality of residues and is further assigned the amino acid type, in the enumerated amino acid type set, of the different residue,
each respective edge in the first plurality of edges uniquely represents a pair of vertices in the first plurality of vertices that are within a threshold distance of each other in the atomic model,
(B) obtaining a primary nuclear Overhauser enhancement (NOE) dataset of a sample comprising the target protein in perdeuterated form, wherein
a second plurality of residues have been isotopically labeled in the sample of the target protein, and
each residue in the second plurality of residues is a member of the enumerated amino acid type set;
(C) identifying a plurality of cross peaks in the primary NOE dataset, wherein each respective cross peak in the primary NOE dataset is generated by NOE interaction between an isotopic label in a different first residue and an isotopic label in a different second residue in the second plurality of residues;
(D) forming a second data construct comprising an observed graph H from the plurality of cross peaks, the observed graph H comprising a second plurality of vertices and a second plurality of edges, wherein
each respective vertex in the second plurality of vertices represents a different residue in the second plurality of residues,
each respective edge in the second plurality of edges represents a corresponding cross peak in the plurality of cross peaks,
each respective vertex in the second plurality of vertices is assigned one or more amino types in the enumerated amino acid type set using amino acid type assignments made by the primary NOE dataset or one or more secondary NOE NMR datasets taken of the target protein;

(E) creating a plurality of placements of the observed graph H onto the original graph G, wherein each respective placement in the plurality of placements (i) includes a plurality of mappings and (ii) maps all the vertices of the observed graph H onto different vertices in the original graph G, each mapping in the plurality of mappings assigning a vertex in the observed graph H to the original graph G, wherein each respective placement in the plurality of placements is subject to a set of constraints comprising:

when a vertex v in the observed graph H is mapped to a vertex w in the original graph G, the amino acid type assigned vertex w in the original graph G is in the one or more amino acid types assigned vertex v, and for an observed edge {a, b} between a vertex a and a vertex b in the observed graph H, when vertex a is mapped to a vertex v and vertex b is mapped to a vertex w in the original graph G, there exists an edge {v, w} between the vertex v and the vertex w in the original graph G;

(F) initializing each set in a plurality of sets, each set in the plurality of sets representing a different vertex in the observed graph H;

(G) determining, for each respective set in the plurality of sets, a number of different mappings for the vertex i represented by the respective set in the observed graph H into the original graph G by polling the plurality of placements as a constraint satisfaction problem in which, for each respective possible assignment of the vertex i into the original graph G, when a determination is made that there exists a mapping in the plurality of mappings that includes the respective assignment, the respective set is advanced, and is not advanced otherwise; and (H) deeming a vertex in the observed graph H to be uniquely assigned to a vertex in the original graph G when the set for the respective vertex includes a single unique assignment upon completion of the determining (G).

16. The method of claim 15, wherein each respective edge in the first plurality of edges is assigned a first edge type when the pair of vertices represented by the respective edge are for a geminal pair of methyls in the atomic model, each respective edge in the first plurality of edges is assigned a second edge type when the pair of vertices represented by the respective edge are not for a geminal pair of methyls in the atomic model, each respective edge in the second plurality of edges is assigned the first edge type or the second edge type, and the set of constraints further comprises the constraint that, when the observed edge {a, b} in the observed graph H is assigned the first edge type, the edge {v, w} in the original graph G is also assigned the first edge type.

17. A computing system for characterizing a target protein or an interaction of the target protein with an entity, the computing system comprising one or more processors and memory storing one or more programs for execution by the one or more processors, the one or more programs singularly or collectively executing a method comprising:

(A) forming a first data construct comprising an original graph G from an atomic model of the target protein, the original graph G comprising a first plurality of vertices and a first plurality of edges, wherein each respective vertex in the first plurality of vertices represents a different residue in the protein, and each respective edge in the first plurality of edges uniquely represents a pair of vertices in the first plurality of vertices that are within a threshold distance of each other in the atomic model, (B) obtaining a primary nuclear Overhauser enhancement (NOE) dataset of a sample comprising the target protein in perdeuterated form, wherein a second plurality of residues have been isotopically labeled in the sample of the target protein, and each residue in the second plurality of residues is a member of the enumerated amino acid type set;

(C) identifying a plurality of cross peaks in the primary NOE dataset, wherein each respective cross peak in the primary NOE dataset is generated by a NOE interaction between an isotopic label in a different first residue and an isotopic label in a different second residue in the second plurality of residues;

(D) forming a second data construct comprising an observed graph H from the plurality of cross peaks, the observed graph H comprising a second plurality of vertices and a second plurality of edges, wherein each respective vertex in the second plurality of vertices represents a different isotopically labeled residue in the protein, and each respective vertex in the second plurality of vertices is assigned one or more amino types using amino acid type assignments made by the primary NOE dataset or one or more secondary NOE NMR datasets taken of the target protein; and (E) evaluating a plurality of placements of the observed graph H onto the original graph G using a constraint satisfaction problem procedure, wherein each respective placement in the plurality of placements (i) includes a plurality of mappings and (ii) maps all the vertices of the observed graph H onto different vertices in the original graph G, each respective mapping in the plurality of mappings assigning a respective vertex in the first plurality of vertices to a corresponding vertex in the second plurality of vertices, each respective placement in the plurality of placements is subject to a set of constraints comprising:

(i) when a vertex v in the observed graph H is mapped to a vertex w in the original graph G, the amino acid type assigned vertex w in the original graph G is in the one or more amino acid types assigned vertex v, and (ii) for an observed edge {a, b} between a vertex a and a vertex b in the observed graph H, when vertex a is mapped to a vertex v and vertex b is mapped to a vertex w in the original graph G, there exists an edge {v, w} between the vertex v and the vertex w in the original graph G;

wherein a respective vertex in the observed graph H is deemed assigned when the constraint satisfaction problem procedure determines that the plurality of placements consists of a single unique assignment for the respective vertex to a corresponding vertex in the original graph G.

18. A method for characterizing a target protein or an interaction of the target protein with an entity, the method comprising:

(A) forming a first data construct comprising an original graph G from an atomic model of the target protein, the original graph G comprising a first plurality of vertices and a first plurality of edges, wherein
  each respective vertex in the first plurality of vertices represents a different residue in the protein, and
  each respective edge in the first plurality of edges uniquely represents a pair of vertices in the first plurality of vertices that are within a threshold distance of each other in the atomic model,
(B) obtaining a primary nuclear Overhauser enhancement (NOE) dataset of a sample comprising the target protein in perdeuterated form, wherein
  a second plurality of residues have been isotopically labeled in the sample of the target protein, and
  each residue in the second plurality of residues is a member of the enumerated amino acid type set;
(C) identifying a plurality of cross peaks in the primary NOE dataset, wherein each respective cross peak in the primary NOE dataset is generated by a NOE interaction between an isotopic label in a different first residue and an isotopic label in a different second residue in the second plurality of residues;
(D) forming a second data construct comprising an observed graph H from the plurality of cross peaks, the observed graph H comprising a second plurality of vertices and a second plurality of edges, wherein each respective vertex in the second plurality of vertices represents a different isotopically labeled residue in the protein, and each respective vertex in the second plurality of vertices is assigned one or more amino types using amino acid type assignments made by the primary NOE dataset or one or more secondary NOE NMR datasets taken of the target protein; and
(E) evaluating a plurality of placements of the observed graph H onto the original graph G using a constraint satisfaction problem procedure, wherein
  each respective placement in the plurality of placements (i) includes a plurality of mappings and (ii) maps all the vertices of the observed graph H onto different vertices in the original graph G, each respective mapping in the plurality of mappings assigning a respective vertex in the first plurality of vertices to a corresponding vertex in the second plurality of vertices,
  each respective placement in the plurality of placements is subject to a set of constraints comprising:
  (i) when a vertex v in the observed graph H is mapped to a vertex w in the original graph G, the amino acid type assigned vertex w in the original graph G is in the one or more amino acid types assigned vertex v, and
  (ii) for an observed edge {a, b} between a vertex a and a vertex b in the observed graph H, when vertex a is mapped to a vertex v and vertex b is mapped to a vertex w in the original graph G, there exists an edge {v, w} between the vertex v and the vertex w in the original graph G;
wherein a respective vertex in the observed graph H is deemed assigned when the constraint satisfaction problem procedure determines that the plurality of placements consists of a single unique assignment for the respective vertex to a corresponding vertex in the original graph G.

* * * * *